(12) United States Patent
Braig et al.

(10) Patent No.: US 6,731,961 B2
(45) Date of Patent: May 4, 2004

(54) METHOD FOR TRANSFORMING PHASE SPECTRA TO ABSORPTION SPECTRA

(75) Inventors: James R. Braig, Piedmont, CA (US); W. Dale Hall, Oakland, CA (US); Casper W. Barnes, Murrieta, CA (US); Peng Zheng, Alameda, CA (US); Jennifer H. Gable, Walnut Creek, CA (US)

(73) Assignee: OptiScan Biomedical Corp., Alameda, CA (US)

( * ) Notice: Subject to any disclaimer, the term of this patent is extended or adjusted under 35 U.S.C. 154(b) by 23 days.

(21) Appl. No.: 10/291,912

(22) Filed: Nov. 8, 2002

(65) Prior Publication Data

US 2003/0133118 A1 Jul. 17, 2003

Related U.S. Application Data

(60) Provisional application No. 60/337,406, filed on Nov. 9, 2001, and provisional application No. 60/340,773, filed on Dec. 11, 2001.

(51) Int. Cl.[7] .................................................. A61B 5/00
(52) U.S. Cl. .................. 600/310; 600/322; 250/339.07; 250/341.6
(58) Field of Search ................................. 600/309, 310, 600/316, 322, 473; 250/341.1, 341.5, 341.6, 339.03, 339.04, 339.05, 339.07, 339.09, 339.12

(56) References Cited

U.S. PATENT DOCUMENTS

| 3,770,958 A | 11/1973 | Krakow |
| 4,819,752 A | 4/1989 | Zelin |
| 4,866,276 A | 9/1989 | Leavens et al. |
| 5,059,394 A | 10/1991 | Phillips et al. |

(List continued on next page.)

FOREIGN PATENT DOCUMENTS

| EP | 0 160 768 | 11/1985 |
| WO | WO 96/01075 | 1/1996 |
| WO | WO 00/53085 | 9/2000 |
| WO | WO 01/30236 | 5/2001 |

OTHER PUBLICATIONS

Klonoff, et al., *Mid–Infrared Spectroscopy for Noninvasive Blood Glucose Monitoring*, http://www.ieee.org/organizations/pubx/newsletter/leos/apr98/midinfr., Apr., 1988, pp. 1–3.

K. Robinson, *Noninvasive Methods Hover on Horizon*, Biophotonics International, May/Jun. 1988, pp. 48–52.

McNichols, et al., *Optical Glucose sensing in biological fluids: an overview*, Journal of Biomedical Optics, Jan. 2000, vol. 5, No. 1, pp. 5–9.

Zheng, et al., *Noninvasive Glucose Determination by Oscillating Thermal Gradient Spectrometry*, Diabetes Technology & Therapeutics, vol. 2, No. 1, 2000, pp. 17–25.

Optics Report, *Glucometry and Diabetes*, pub. by Breault Research Organization, www.OpticsReport.com, vol. 1, Issue 2, May 2001, pp. 1–4.

*Primary Examiner*—Eric F. Winakur
(74) *Attorney, Agent, or Firm*—Knobbe Martens Olson & Bear LLP

(57) ABSTRACT

A device and method for determining analyte concentrations within a material sample are provided. A modulating temperature gradient is induced in the sample and resultant, emitted infrared radiation is measured at selected analyte absorbance peaks and reference wavelengths. The modulating temperature gradient is controlled by a surface temperature modulation. One embodiment provides a transfer function relating the surface temperature modulation to a modulation of the measured infrared radiation. Phase and magnitude differences in the transfer function are detected in the presence of the sought-after analyte. These phase and magnitude differences, having a relationship to analyte concentration, are measured, correlated and processed to determine analyte concentration in the material sample. Another embodiment provides a method for transforming thermal phase spectra to absorption spectra for consistent determination of analyte concentration within the sample.

24 Claims, 18 Drawing Sheets

U.S. PATENT DOCUMENTS

| | | |
|---|---|---|
| 5,070,242 A | 12/1991 | McClelland et al. |
| 5,070,874 A | 12/1991 | Barnes et al. |
| 5,115,133 A | 5/1992 | Knudson |
| 5,146,091 A | 9/1992 | Knudson |
| 5,313,941 A | 5/1994 | Braig et al. |
| 5,324,979 A | 6/1994 | Rosenthal |
| 5,337,745 A | 8/1994 | Benaron |
| 5,379,764 A | 1/1995 | Barnes et al. |
| 5,515,847 A | 5/1996 | Braig et al. |
| 5,606,164 A | 2/1997 | Price et al. |
| 5,615,672 A | 4/1997 | Braig et al. |
| 5,657,754 A | 8/1997 | Rosencwaig |
| 5,747,806 A | 5/1998 | Khalil et al. |
| 5,823,677 A | 10/1998 | Forester et al. |
| 5,877,500 A | 3/1999 | Braig et al. |
| 5,900,632 A | 5/1999 | Sterling et al. |
| 6,025,597 A | 2/2000 | Sterling et al. |
| 6,049,081 A | 4/2000 | Sterling et al. |
| 6,072,180 A | 6/2000 | Kramer et al. |
| 6,097,975 A | 8/2000 | Petrovsky et al. |
| 6,157,041 A | 12/2000 | Thomas et al. |
| 6,161,028 A | 12/2000 | Braig et al. |
| 6,196,046 B1 | 3/2001 | Braig et al. |
| 6,198,949 B1 | 3/2001 | Braig et al. |
| 6,246,892 B1 | 6/2001 | Chance |
| 6,264,622 B1 | 7/2001 | Augustine |

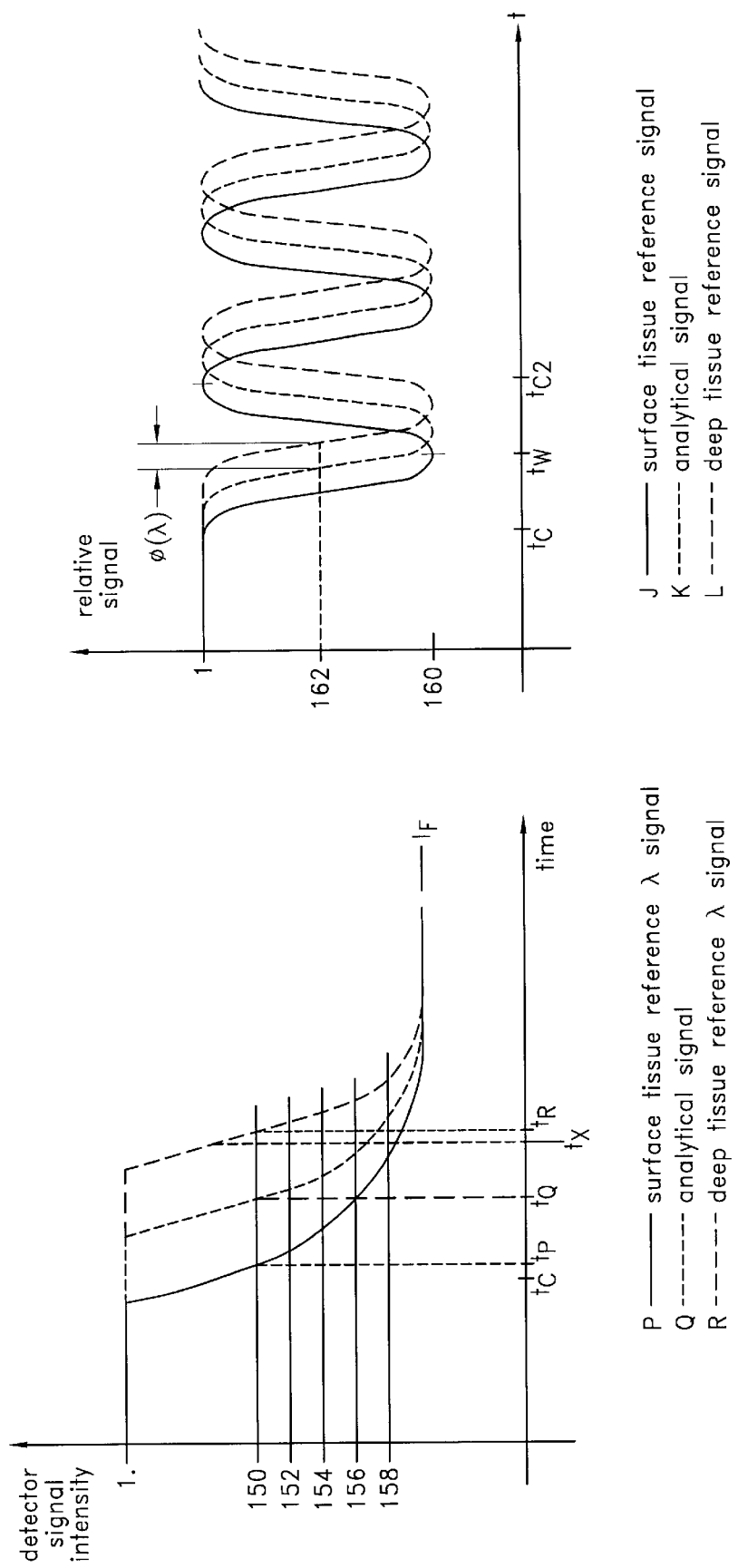

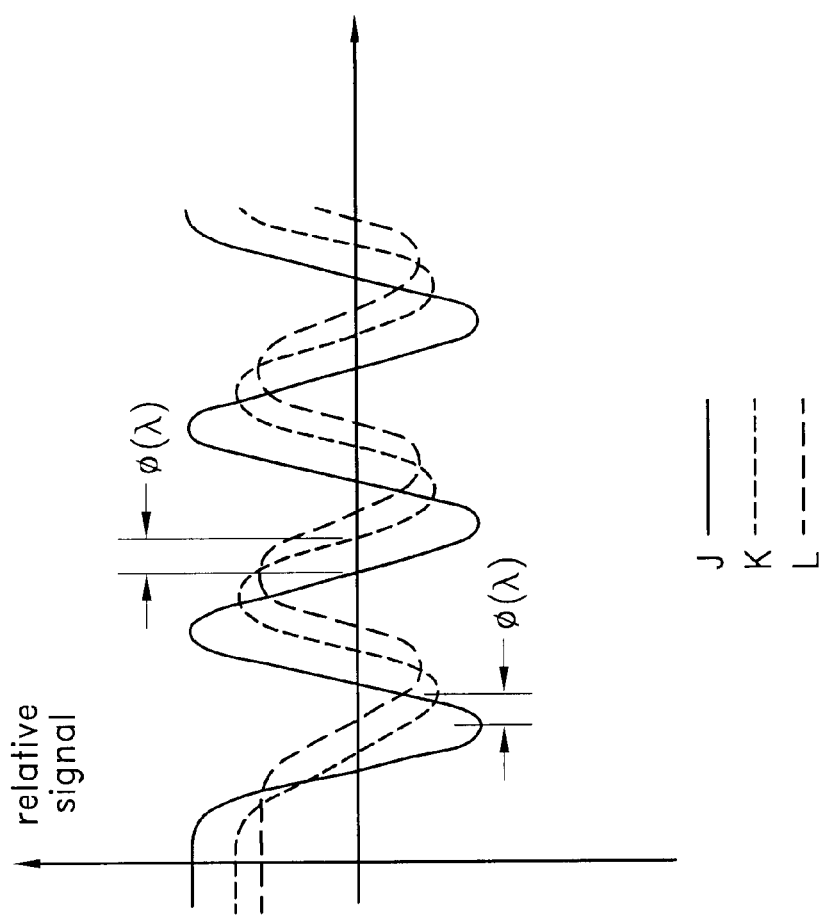

— Reference Signal G
— Analytical Signal H

METHOD FOR TRANSFORMING PHASE SPECTRA TO ABSORPTION SPECTRA

RELATED APPLICATIONS

This application claims priority to U.S. Provisional Patent Applications No. 60/337,406, filed Nov. 9, 2001 and Ser. No. 60/340,773, filed Dec. 11, 2001, both entitled METHOD FOR TRANSFORMING PHASE SPECTRA TO ABSORPTION SPECTRA, the entire contents of both of which are hereby incorporated by reference.

BACKGROUND OF THE INVENTION

1. Field of the Invention

The disclosure herein relates generally to determining analyte concentrations within a material sample.

2. Description of the Related Art

Millions of diabetics are forced to draw blood on a daily basis to determine their blood glucose levels. In addition, the detection of other blood constituents, such as the determination of the concentration of alcohol in the bloodstream, often requires blood withdrawal in order to perform a precise analysis thereof. A search for a noninvasive methodology to accurately determine blood constituent levels has been substantially expanded in order to alleviate the discomfort of these individuals. A significant advance in the state of the art of noninvasive blood constituent analysis has been realized by the development of spectrometers, including "thermal gradient" spectrometers, which analyze the absorbance of particular wavelengths of infrared energy passed through and/or emitted by a sample of tissue. These spectroscopic analytical devices typically employ a window or lens for admitting infrared spectra into the device for analysis by infrared detectors.

Although these devices have marked a significant advance in the state of the art of noninvasive blood constituent analysis, further improvements could be made in the performance and ease of manufacture of such devices.

SUMMARY OF THE INVENTION

A device and method for determining analyte concentrations within a material sample are provided. A modulating temperature gradient is induced in the sample and resultant, emitted infrared radiation is measured at selected analyte absorbance peaks and reference wavelengths. The modulating temperature gradient is controlled by a surface temperature modulation. One embodiment provides a transfer function relating the surface temperature modulation to a modulation of the measured infrared radiation. Phase and magnitude differences in the transfer function are detected in the presence of the sought-after analyte. These phase and magnitude differences, having a relationship to analyte concentration, are measured, correlated and processed to determine analyte concentration in the material sample. Another embodiment provides a method for transforming thermal phase spectra to absorption spectra for consistent determination of analyte concentration within the sample.

In one embodiment, a method is provided for determining a concentration of an analyte within a material sample. The material sample is induced to emit electromagnetic energy in a time-varying manner. The induced electromagnetic energy emitted by the material sample is measured at at least one wavelength, wherein the measuring comprises analyzing the material sample with an optical measurement system. A phase of the electromagnetic energy is determined and then converted into an absorption value. The concentration of the analyte is then determined based at least in part on the absorption value.

In another embodiment, a method is provided for determining a concentration of an analyte within a material sample. At least a portion of a phase spectrum is determined based on electromagnetic energy emitted by the material sample. The at least a portion of the phase spectrum is converted into at least a portion of an absorption spectrum. The concentration is determined based on the at least a portion of the absorption spectrum.

In one embodiment, an analyte detection system is provided. The analyte detection system comprises a detector array, a processing circuit in communication with the detector array, and a module. The module is executable by the processing circuit whereby the processing circuit converts a phase spectrum, based on electromagnetic energy emitted by a material sample and measured by the detector array, into an absorption spectrum and determines a concentration of an analyte within the material sample based on the absorption spectrum.

In another embodiment, a method of estimating analyte concentration in a sample is provided. A time varying temperature is applied to a portion of a sample. Time varying infrared radiation intensity received from the sample is measured in at least one wavelength band. An absorption coefficient a is calculated in the wavelength band based at least in part on the time varying infrared radiation intensity received from the sample.

BRIEF DESCRIPTION OF THE DRAWINGS

FIG. 8 depicts a first methodology for determining the concentration of an analyte of interest.

FIG. 9 depicts a second methodology for determining the concentration of an analyte of interest.

FIG. 10 depicts a third methodology for determining the concentration of an analyte of interest.

DETAILED DESCRIPTION OF THE PREFERRED EMBODIMENTS

Figure 1:
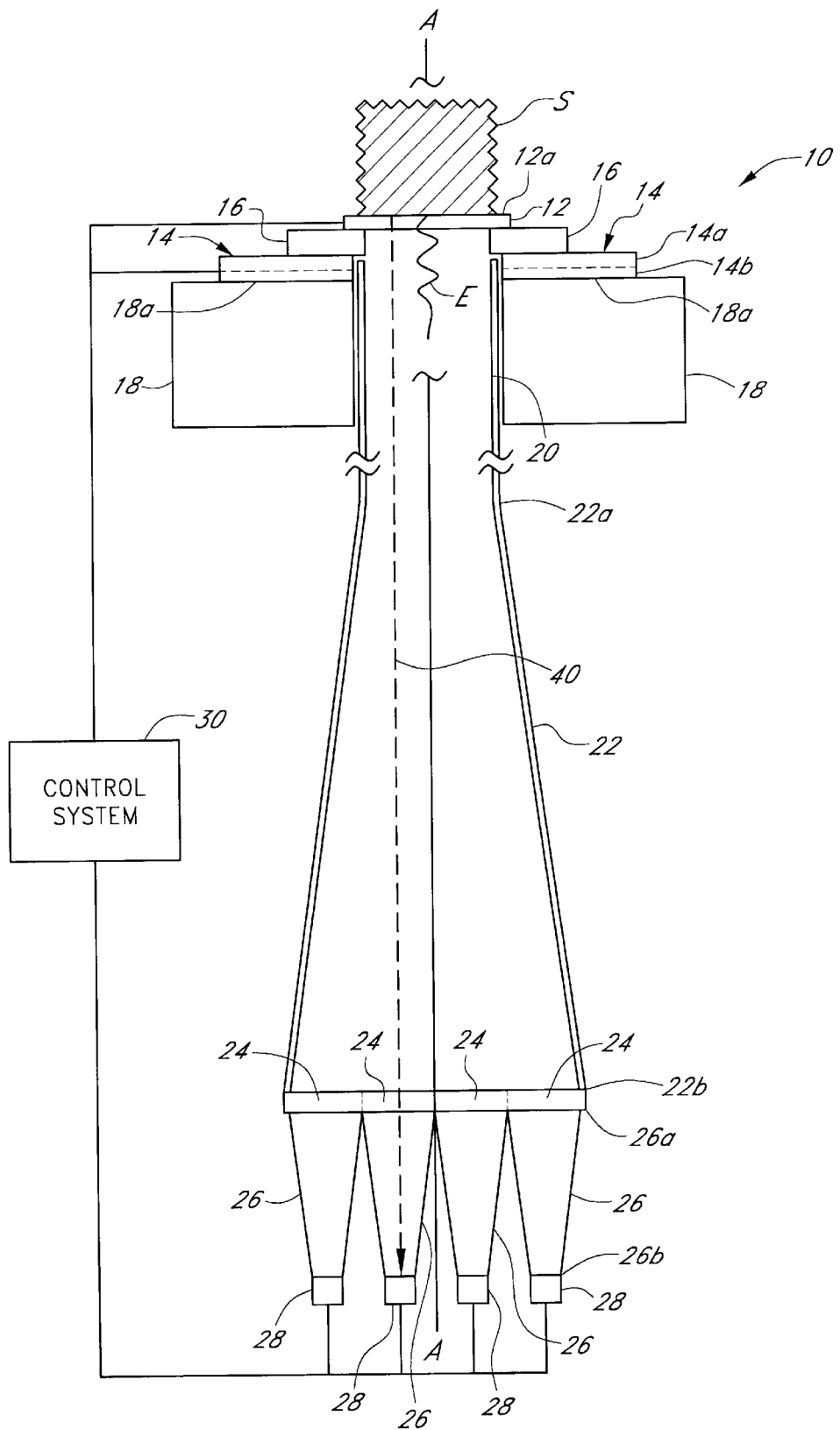
FIG. 1 is a schematic view of a noninvasive optical detection system.

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

The methods and embodiments discussed herein are particularly suited for use with an apparatus taught in Assignee's U.S. Pat. No. 6,198,949, titled SOLID-STATE NONINVASIVE INFRARED ABSORPTION SPECTROMETER FOR THE GENERATION AND CAPTURE OF THERMAL GRADIENT SPECTRA FROM LIVING TISSUE, issued Mar. 6, 2001; and with the methodology taught in Assignee's U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; as well as with the methods and apparatus taught in Assignee's U.S. patent applications Ser. No. 09/538,164, entitled METHOD AND APPARATUS FOR DETERMINING ANALYTE CONCENTRATION USING PHASE AND MAGNITUDE DETECTION OF A RADIATION TRANSFER FUNCTION; and Ser. No. 60/340,773, filed on Dec. 11, 2001, entitled METHOD FOR TRANSFORMING PHASE SPECTRA TO ABSORPTION SPECTRA. The entire disclosure of all of the above-mentioned patents and patent applications are hereby incorporated by reference herein and made a part of this specification.

I. OVERVIEW OF ANALYTE DETECTION SYSTEMS

Disclosed herein are analyte detection systems, including a noninvasive system discussed largely in part A below and a whole-blood system discussed largely in part B below. Also disclosed are various methods, including methods for detecting the concentration of an analyte in a material sample. Both the noninvasive system/method and the whole-blood system/method can employ optical measurement. As used herein with reference to measurement apparatus and methods, "optical" is a broad term and is used in its ordinary sense and refers, without limitation, to identification of the presence or concentration of an analyte in a material sample by measuring properties related to the sample's emission, absorption, or other form of interaction with electromagnetic energy. As discussed in more detail below, the two approaches each can operate independently to perform an optical analysis of a material sample. The two approaches can also be combined in an apparatus, or the two approaches can be used together to perform different steps of a method.

The two approaches may be combined to perform calibration of an apparatus, e.g., of an apparatus that employs a noninvasive approach. In another embodiment, an advantageous combination of the two approaches performs an invasive measurement to achieve greater accuracy and a non-invasive measurement to minimize discomfort to the patient. For example, the invasive (also sometimes referred to as a whole-blood technique) may be more accurate than the noninvasive technique at certain times of the day, e.g., at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) in question.

A. Noninvasive System

1. Monitor Structure

FIG. 1 depicts a noninvasive optical detection system which is especially adapted for non-invasive measurements (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" (or, alternatively, "traditional") is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but not are limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared-energy when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
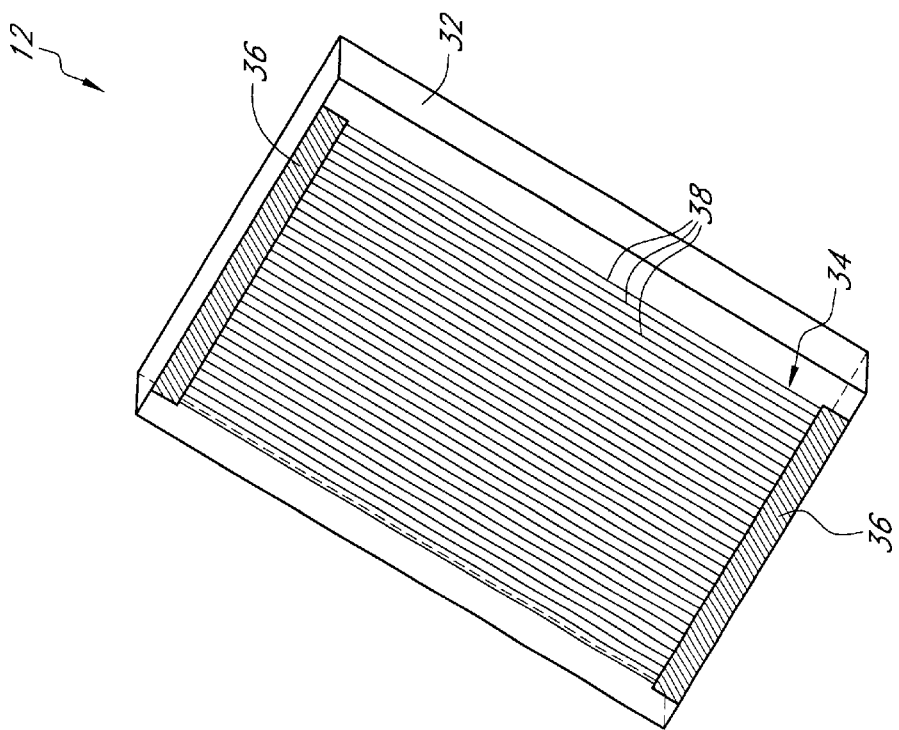
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices (RTDs), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those or ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire layer 34. Where a constant pitch distance is employed, the preferred distance is at least about 50–100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency (RF) heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 32 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 2A:
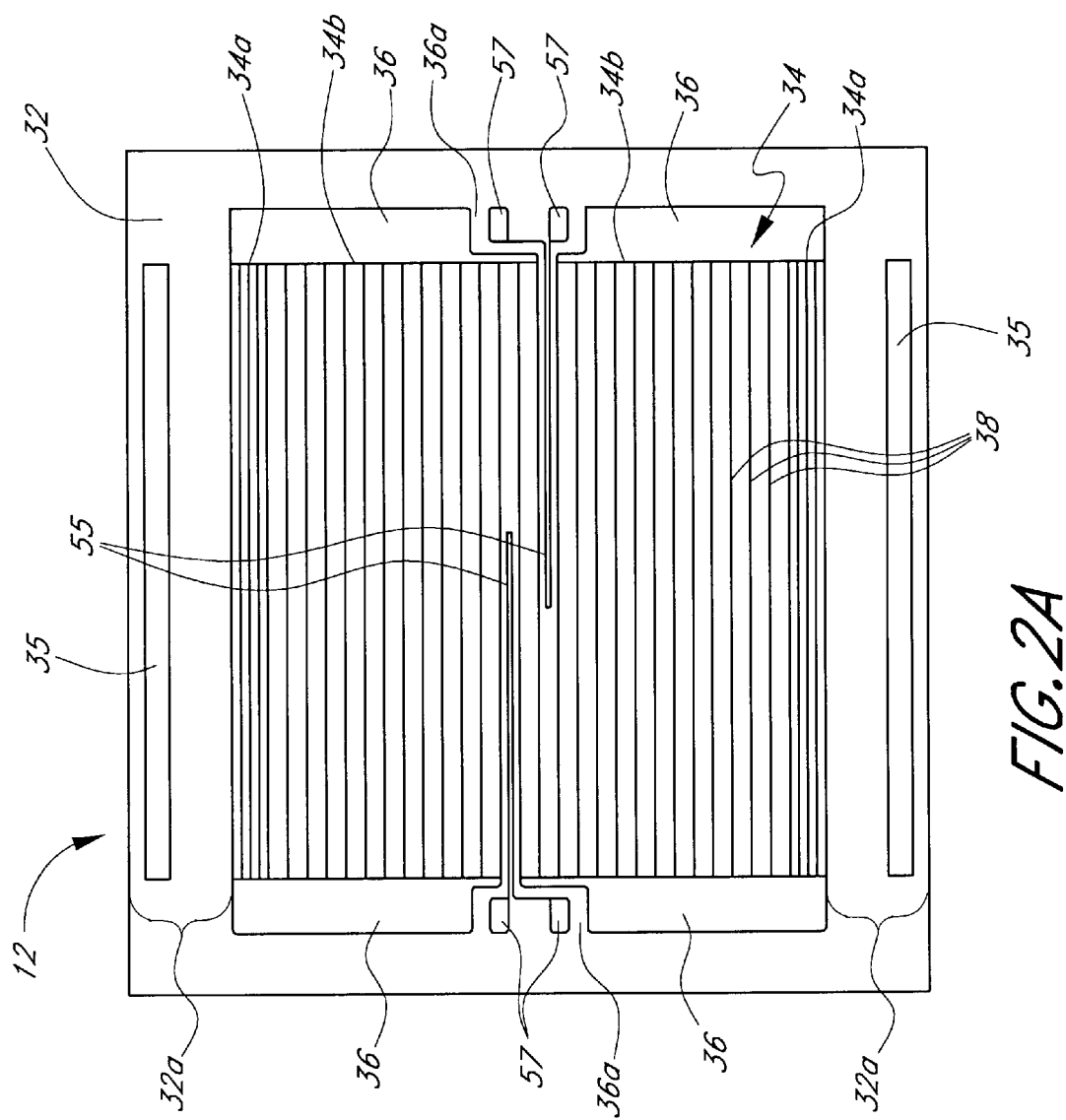
FIG. 2A is a plan view of another embodiment of a window assembly for use with the noninvasive detection system.

FIG. 2A shows another embodiment of the window assembly 12, that may be used in place of the window assembly 12 depicted in FIG. 2. The window assembly 12 shown in FIG. 2A may be similar to that shown in FIG. 2, except as described below. In the embodiment of FIG. 2A the main layer 32 has a preferred thickness of up to about 0.012" and more preferably about 0.010" or less. The heater layer 34 may also include one or more resistance temperature devices (RTD's) 55 to measure the temperature of the window assembly 12 and provide temperature feedback to a control system 30. The RTDs 55 terminate in RTD connection pads 57.

In the embodiment of FIG. 2A, the heater elements 38 are typically provided with a width of about 25 microns. The pitch distance separating centerlines of adjacent heater elements 38 may be reduced, and/or the width of the heater elements 38 may be increased, in the regions of the window assembly 12 near the point(s) of contact with the thermal diffuser 410 (see FIGS. 6B–6D and discussion below). This arrangement advantageously promotes an isothermal temperature profile at the upper surface of the main layer 32 despite thermal contact with the thermal diffuser.

The embodiment shown in FIG. 2A includes a plurality of heater elements 38 of substantially equal width which are variably spaced across the width of the main layer 32. In the embodiment of FIG. 2A, the centerlines of the heater elements 38 are spaced at a first pitch distance of about 0.0070" at peripheral portions 34a of the heater layer 34, and at a second pitch distance of about 0.015" at a central portion 34b of the main layer 32. The heater elements 38 closest to the center are preferably sufficiently spaced to allow the RTDs 55 to extend therebetween. In the embodiment of FIG. 2A, the main layer 32 includes peripheral regions 32a which extend about 0.053" from the outermost heater element on each side of the heater layer 34 to the adjacent edge of the main layer 32. As shown, the bus bars 36 are preferably configured and segmented to allow space for the RTDs 55 and the RTD connection pads 57, in intermediate gaps 36a. The RTDs 55 preferably extend into the array of heater elements 38 by distance that is slightly longer than half of the length of an individual heater element 38. In alternative embodiments, the RTDs 55 may be located at the edges of the main layer 32, or at other locations as desired for a particular noninvasive system.

With continued reference to FIG. 2A, the peripheral regions of the main layer 32 may include metallized edge portions 35 for facilitating connection to the diffuser 410 (discussed below in connection with FIGS. 6B–6D). The metallized edge portions 35 may be formed by the same or similar processes used in forming the heater elements 38 and RTDs 55. In the embodiment of FIG. 2A, the edge portions 35 are typically between about 0.040" and about 0.060" wide by about 0.450" and about 0.650" long, and in one embodiment, they are about 0.050" by about 0.550". Other dimensions may be appropriately used so long as the window assembly 12 may be joined in thermal communication with the diffuser 410 as needed.

In the embodiment shown in FIG. 2A, the main layer 32 is about 0.690" long by about 0.571" wide, and the heater layer (excluding the metallized edge portions 35) is about 0.640" long by about 0.465" wide. The main layer 32 is about 0.010"–0.012" thick, and is advantageously thinner than about 0.010" where possible. Each heater element 38 is about 0.570" long, and each peripheral region 34a is about 0.280" wide. These dimensions are merely exemplary; of course, other dimensions may be used as desired.

Figure 3:
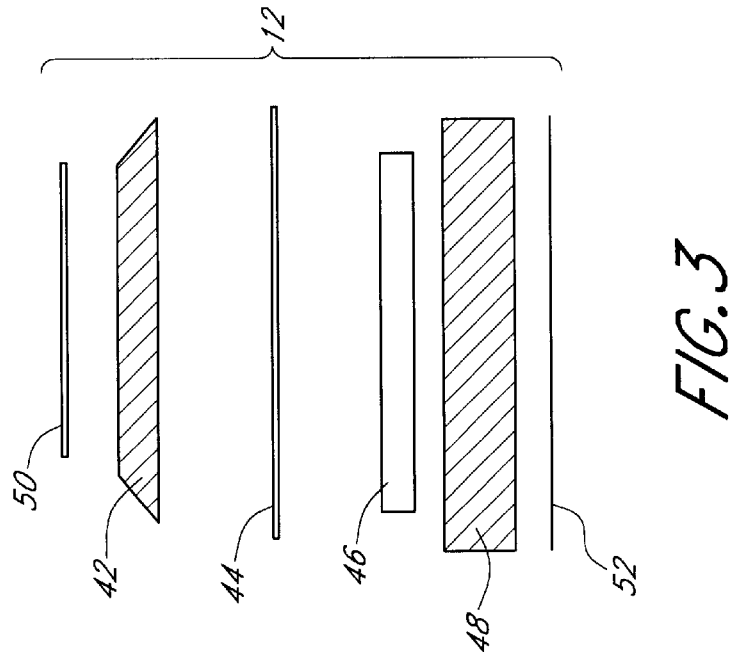
FIG. 3 is an exploded schematic view of another embodiment of a window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is a thermal insulating and impedance matching layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamondlike carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective layer 50 is intended to protect the top surface of the spreader layer 42 from damage. Ideally, the protective layer is highly infrared-transmissive and highly resistant to mechanical damage, such as scratching or abrasion. It is also preferred that the protective layer 50 and the overcoat layer 52 have high thermal conductivity and antireflective and/or index-matching properties. A satisfactory material for use as the protective layer 50 and the overcoat layer 52 is the multi-layer Broad Band Anti-Reflective Coating produced by Deposition Research Laboratories, Inc. of St. Charles, Mo. Diamondlike carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1,500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater element 44 while allowing the cooling system 14 to effectively cool the material sample S (see FIG. 1). This layer 46 comprises a material having thermally insulative (e.g., lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Tex. The pictured embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 5:
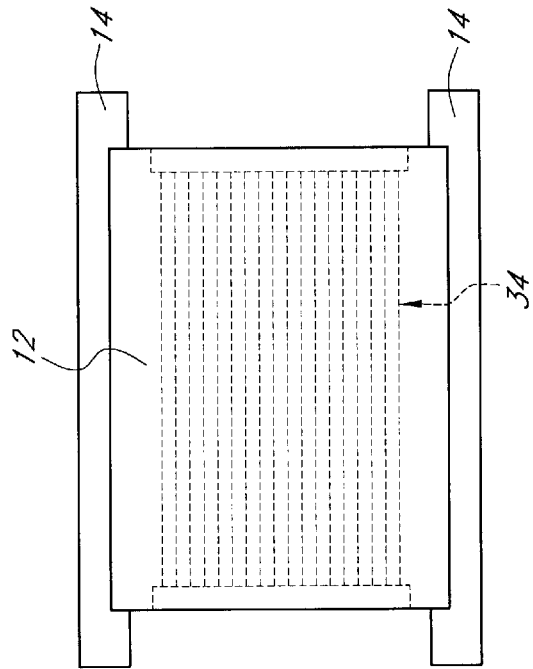
FIG. 5 is a plan view of the window assembly connected to a cold reservoir.
Figure 4:
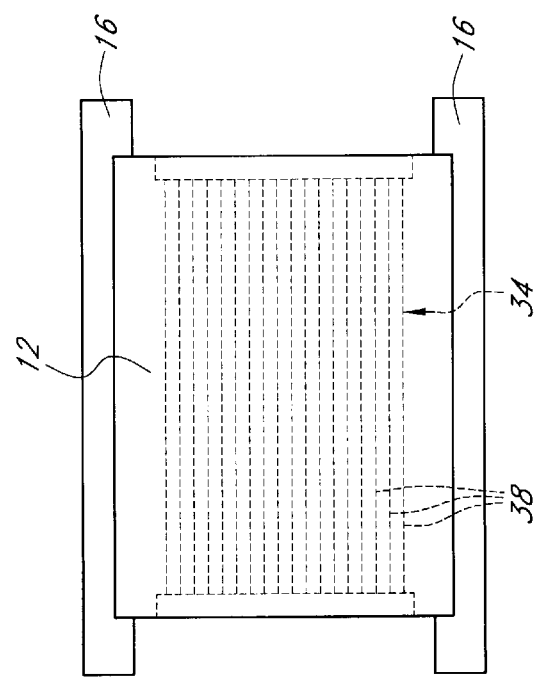
FIG. 4 is a plan view of the window assembly connected to a cooling system.

FIG. 4 is a top schematic view of a preferred arrangement of the window assembly 12 (of the types shown in FIG. 2 or 2A) and the cold reservoir 16, and FIG. 5, is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. In order to promote a substantially uniform or isothermal temperature profile over the upper surface of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

The heat sink 18 drains waste heat from the hot surface 14b of the cooling system 16 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 18, is in thermally conductive relation to the hot surface 14b of the cooling system 14 (see FIG. 1). A cavity 54 is formed in the heat sink 18 and preferably contains a phase-change material (not shown) to increase the capacity of the sink 18. A preferred phase change material is a hydrated salt, such as calciumchloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and nonabsorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, etc.

c. Window Mounting System

Figure 6A:
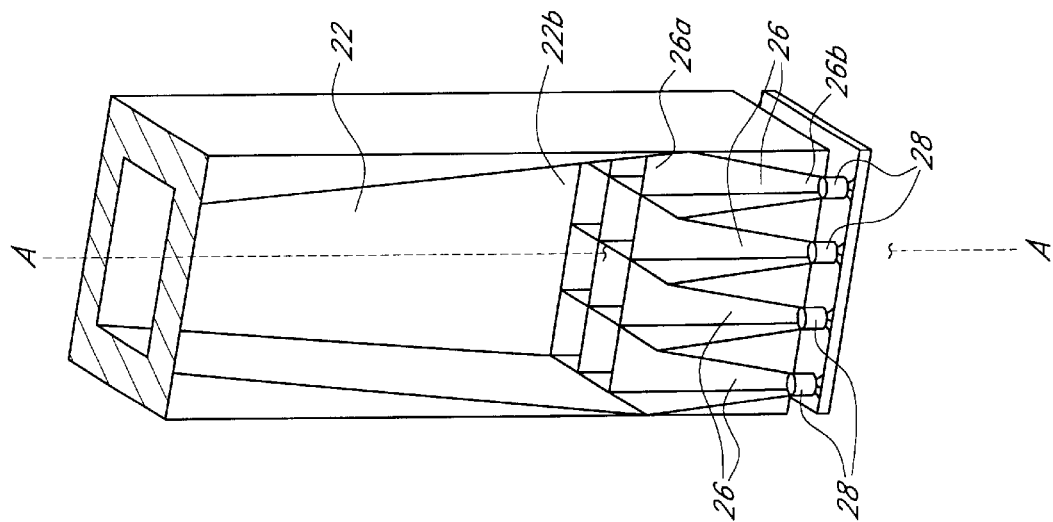
FIG. 6A is a cutaway perspective view of a lower portion of the noninvasive detection system of FIG. 1.
Figure 6:
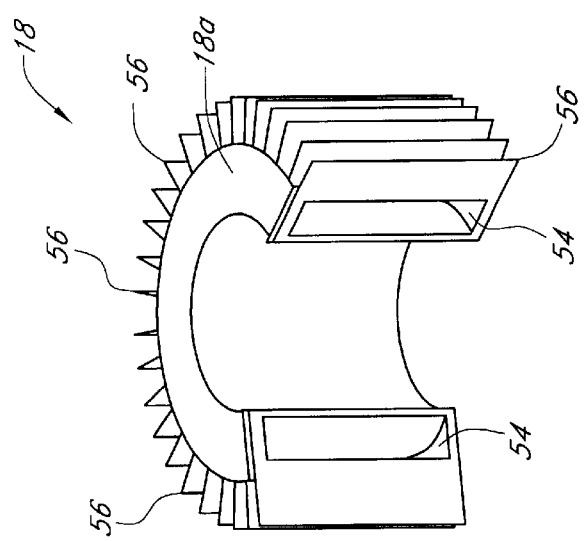
FIG. 6 is a cutaway view of a heat sink for use with the noninvasive detection system.
Figure 6B:
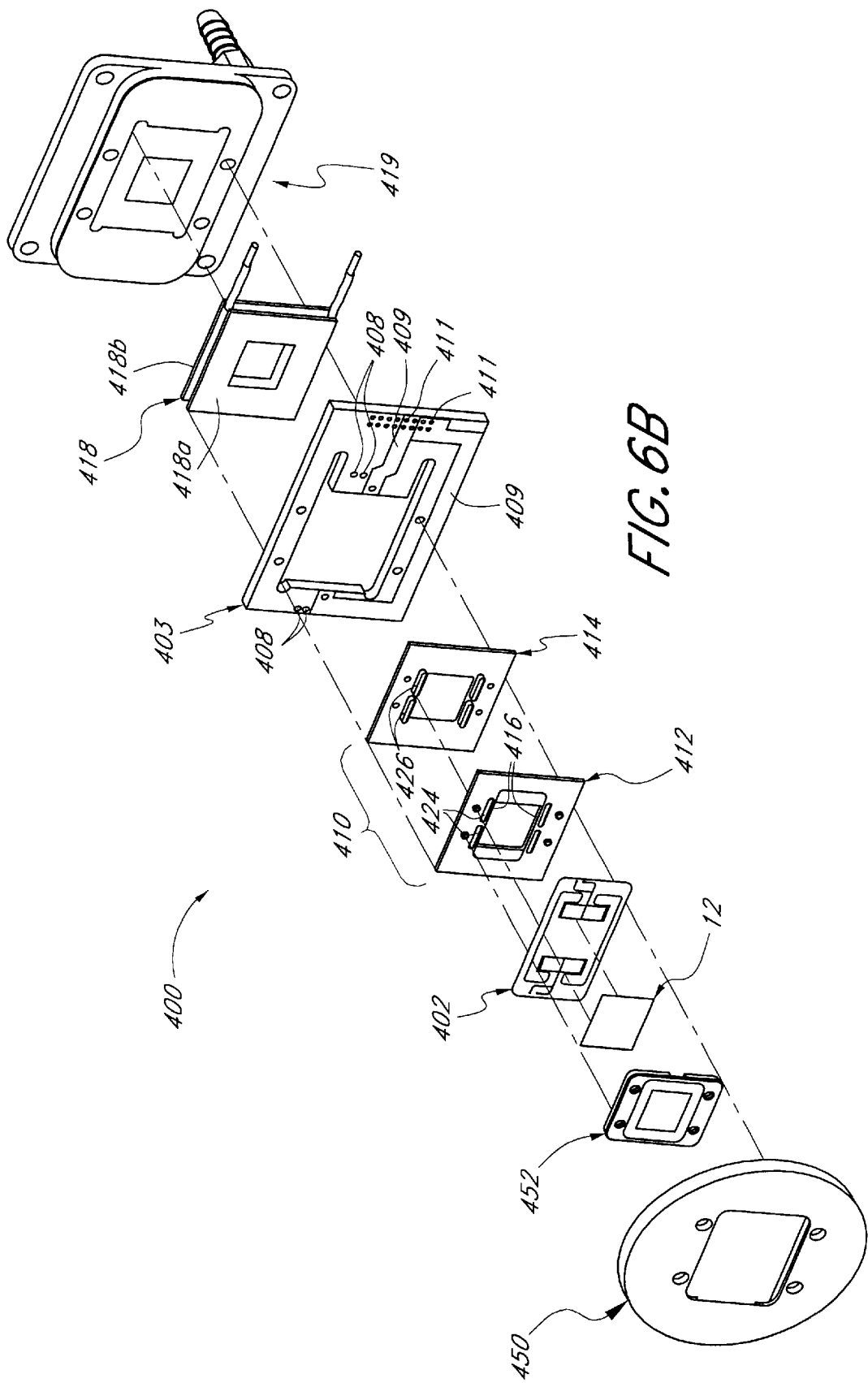
FIG. 6B is an exploded perspective view of a window mounting system for use with the noninvasive optical detection system.

FIG. 6B illustrates an exploded view of a window mounting system 400 which, in one embodiment, is employed as part of the noninvasive system 10 disclosed above. Where employed in connection with the noninvasive system 10, the window mounting system 400 supplements or, where appropriate, replaces any of the window assembly 12, cooling system 14, cold reservoir 16 and heat sink 18 shown in FIG. 1. In one embodiment, the window mounting system 400 is employed in conjunction with the window assembly 12 depicted in FIG. 2A; in alternative embodiments, the window assemblies shown in FIGS. 2 and 3 and described above may also be used in conjunction with the window mounting system 400 illustrated in FIG. 6B.

In the window mounting system 400, the window assembly 12 is physically and electrically connected (typically by soldering) to a first printed circuit board ("first PCB") 402. The window assembly 12 is also in thermally conductive relation (typically by contact) to a thermal diffuser 410. The window assembly may also be fixed to the diffuser 410 by soldering.

The thermal diffuser 410 generally comprises a heat spreader layer 412 which, as mentioned, preferably contacts the window assembly 12, and a conductive layer 414 which is typically soldered to the heat spreader layer 412. The conductive layer 414 may then be placed in direct contact with a cold side 418a of a thermoelectric cooler (TEC) 418 or other cooling device. The TEC 418, which in one embodiment comprises a 25 W TEC manufactured by MELCOR, is in electrical communication with a second PCB 403, which includes TEC power leads 409 and TEC power terminals 411 for connection of the TEC 418 to an appropriate power source (not shown). The second PCB 403 also includes contacts 408 for connection with RTD terminals 407 (see FIG. 6C) of the first PCB 402. A heat sink 419, which may take the form of the illustrated water jacket, the heat sink 18 shown in FIG. 6, any other heat sink structures mentioned herein, or any other appropriate device, is in thermal communication with a hot side 418b of the TEC 418 (or other cooling device), in order to remove any excess heat created by the TEC 418.

Figure 6C:
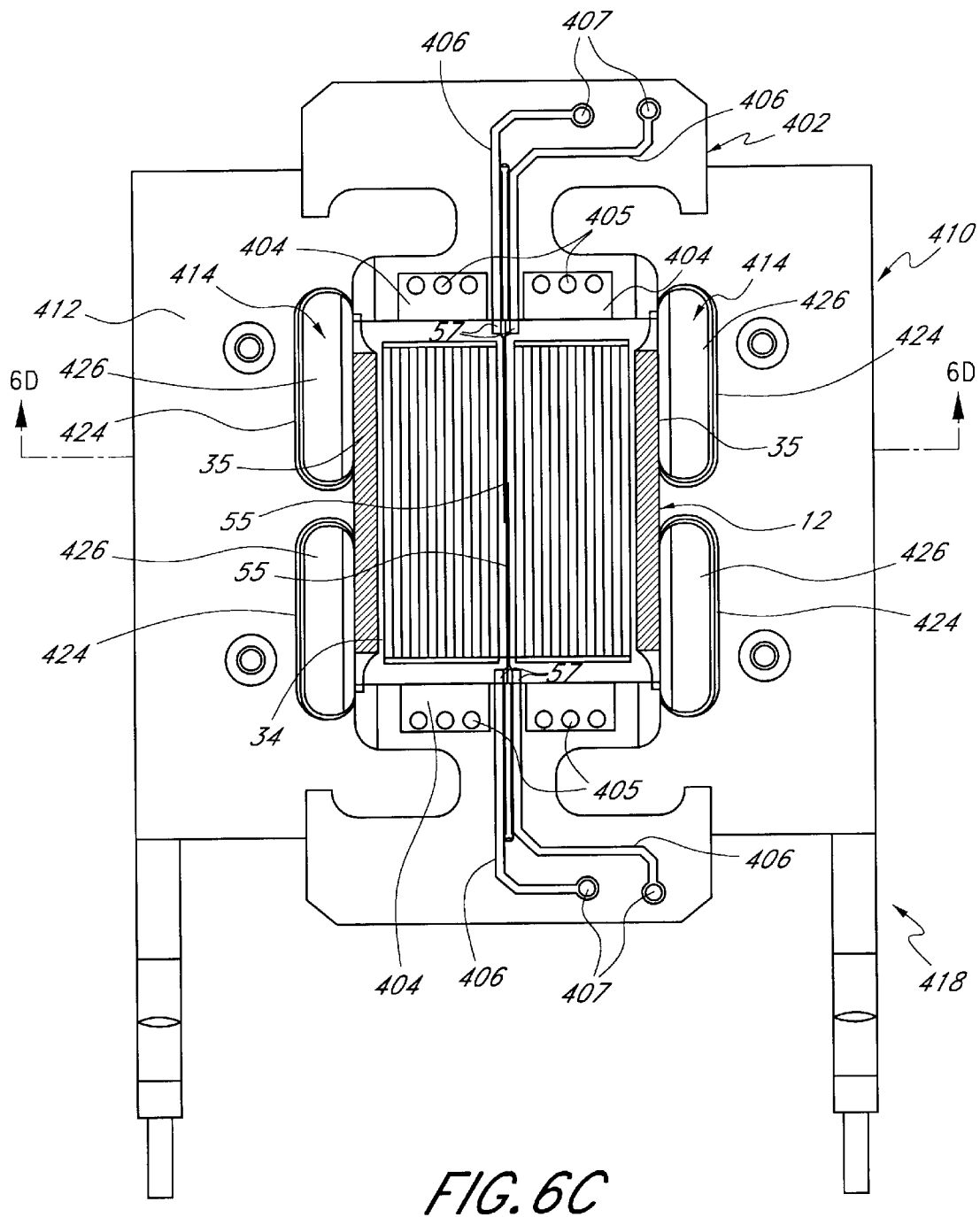
FIG. 6C is a partial plan view of the window mounting system of FIG. 6B.

FIG. 6C illustrates a plan view of the interconnection of the window assembly 12, the first PCB 402, the diffuser 410 and the thermoelectric cooler 418. The first PCB includes RTD bonding leads 406 and heater bonding pads 404 which permit attachment of the RTDs 55 and bus bars 36, respectively, of the window assembly 12 to the first PCB 402 via soldering or other conventional techniques. Electrical communication is thus established between the heater elements 38 of the heater layer 34, and heater terminals 405 formed in the heater bonding pads 404. Similarly, electrical communication is established between the RTDs 55 and RTD terminals 407 formed at the ends of the RTD bonding leads 406. Electrical connections can be established with the heater elements 38 and the RTDs 55 via simple connection to the terminals 405, 407 of the first PCB 402.

With further reference to FIGS. 2A and 6B–6C, the heat spreader layer 412 of the thermal diffuser 410 contacts the underside of the main layer 32 of the window assembly 12 via a pair of rails 416. The rails 416 may contact the main layer 32 at the metallized edge portions 35, or at any other appropriate location. The physical and thermal connection between the rails 416 and the window main layer 32 may be achieved by soldering, as indicated above. Alternatively, the connection may be achieved by an adhesive such as epoxy, or any other appropriate method. The material chosen for the window main layer 32 is preferably sufficiently thermally conductive that heat may be quickly removed from the main layer 32 through the rails 416, the diffuser 410, and the TEC 128.

Figure 6D:
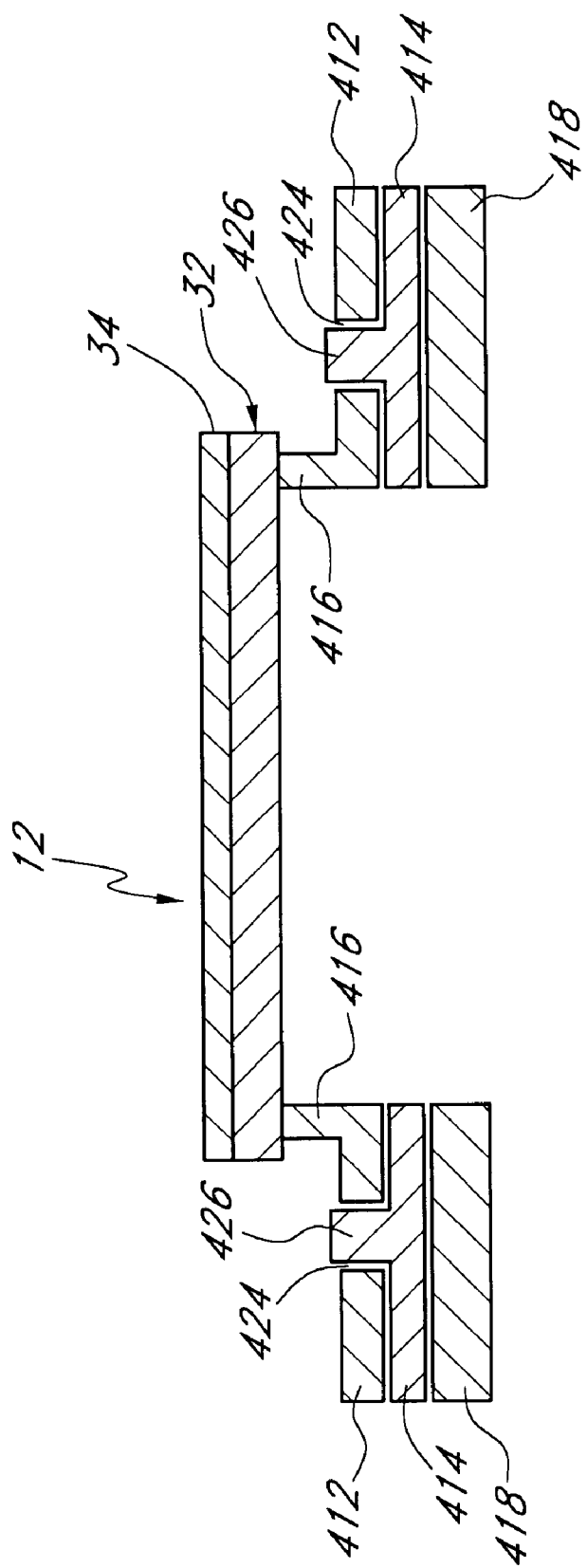
FIG. 6D is a sectional view of the window mounting system of FIG. 6C.

FIG. 6D shows a cross-sectional view of the assembly of FIG. 6C through line 22—22. As can be seen in FIG. 6D, the window assembly 12 contacts the rails 416 of the heat spreader layer 412. The conductive layer 414 underlies the spreader layer 412 and may comprise protrusions 426 configured to extend through openings 424 formed in the spreader layer 412. The openings 424 and protrusions 426 are sized to leave sufficient expansion space therebetween, to allow expansion and contraction of the conductive layer 414 without interference with, or causing deformation of, the window assembly 12 or the heat spreader layer 412. Moreover, the protrusions 426 and openings 424 coact to prevent displacement of the spreader layer 412 with respect to the conductive layer 414 as the conductive layer 414 expands and contracts.

The thermal diffuser 410 provides a thermal impedance between the TEC 418 and the window assembly 12, which impedance is selected to drain heat from the window assembly at a rate proportional to the power output of the heater layer 34. In this way, the temperature of the main layer 32 can be rapidly cycled between a "hot" and a "cold" temperatures, thereby allowing a time-varying thermal gradient to be induced in a sample S placed against the window assembly 12.

The heat spreader layer 412 is preferably made of a material which has substantially the same coefficient of thermal expansion as the material used to form the window assembly main layer 32, within the expected operating temperature range. Preferably, both the material used to form the main layer 32 and the material used to form the heat spreader layer 412 have substantially the same, extremely low, coefficient of thermal expansion. For this reason, CVD diamond is preferred for the main layer 32 (as mentioned above); with a CVD diamond main layer 32 the preferred material for the heat spreader layer 412 is Invar. Invar advantageously has an extremely low coefficient of thermal expansion and a relatively high thermal conductivity. Because Invar is a metal, the main layer 32 and the heat spreader layer 412 can be thermally bonded to one another with little difficulty. Alternatively, other materials may be used for the heat spreader layer 412; for example, any of a number of glass and ceramic materials with low coefficients of thermal expansion may be employed.

The conductive layer 414 of the thermal diffuser 410 is typically a highly thermally conductive material such as copper (or, alternatively, other metals or non-metals exhibiting comparable thermal conductivities). The conductive layer 414 is typically soldered or otherwise bonded to the underside of the heat spreader layer 412.

In the illustrated embodiment, the heat spreader layer 412 may be constructed according to the following dimensions, which are to be understood as exemplary; accordingly the dimensions may be varied as desired. The heat spreader layer 412 has an overall length and width of about 1.170", with a central opening of about 0.590" long by 0.470" wide.

Generally, the heat spreader layer 412 is about 0.030" thick; however, the rails 416 extend a further 0.045" above the basic thickness of the heat spreader layer 412. Each rail 416 has an overall length of about 0.710"; over the central 0.525" of this length each rail 416 is about 0.053" wide. On either side of the central width each rail 416 tapers, at a radius of about 0.6", down to a width of about 0.023". Each opening 424 is about 0.360" long by about 0.085" wide, with corners rounded at a radius of about 0.033".

In the illustrated embodiment, conductive layer 414 may be constructed according to the following dimensions, which are to be understood as exemplary; accordingly the dimensions may be varied as desired. The conductive layer 414 has an overall length and width of about 1.170", with a central opening of about 0.590" long by 0.470" wide. Generally, the conductive layer 412 is about 0.035" thick; however, the protrusions 426 extend a further 0.075"-0.085" above the basic thickness of the conductive layer 414. Each protrusion 426 is about 0.343" long by about 0.076" wide, with corners rounded at a radius of about 0.035".

As shown in FIG. 6B, first and second clamping plates 450 and 452 may be used to clamp the portions of the window mounting system 400 to one another. For example, the second clamping plate 452 is configured to clamp the window assembly 12 and the first PCB 402 to the diffuser 410 with screws or other fasteners extending through the openings shown in the second clamping plate 452, the heat spreader layer 412 and the conductive layer 414. Similarly, the first clamping plate 450 is configured overlie the second clamping plate 452 and clamp the rest of the window mounting system 400 to the heat sink 419, thus sandwiching the second clamping plate 452, the window assembly 12, the first PCB 402, the diffuser 410, the second PCB 403, and the TEC 418 therebetween. The first clamping plate 450 prevents undesired contact between the sample S and any portion of the window mounting system 400, other than the window assembly 12 itself. Other mounting plates and mechanisms may also be used as desired.

d. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A—A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A—A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is be advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A—A. The collimator 22 aligns the infrared energy E to propagate in a direction that is generally parallel to the longitudinal axis A—A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A—A) of about 0–15 degrees before the energy E impinges upon the filters 24. Of course, other dimensions or incidence angles may be employed in constructing and operating the collimator 22.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective.

Preferably, the concentrators 26 have a rectangular cross-section (as taken orthogonal to the longitudinal axis A—A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the collimators 26 are substantially straight and form an angle of about 8 degrees with respect to the longitudinal axis A—A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

e. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 µm±0.03 µm, 8.40 µm ±0.03 µm, 9.48 µm±0.04 µm, and 11.10 µm ±0.04 µm, respectively, which correspond to wavelengths around which water and glucose absorb electromagnetic radiation. Typical bandwidths for these filters range from 0.20 µm to 0.50 µm.

In an alternative embodiment, the array of wavelength-specific filters 24 may be replaced with a single Fabry-Perot interferometer, which can provide wavelength sensitivity which varies as a sample of infrared energy is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

f. Detectors

The detectors 28 may comprise any detector type suitable for sensing infrared energy, preferably in the mid-infrared wavelengths. For example, the detectors 28 may comprise mercury-cadmium-telluride (MCT) detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

g. Control System

Figure 7:
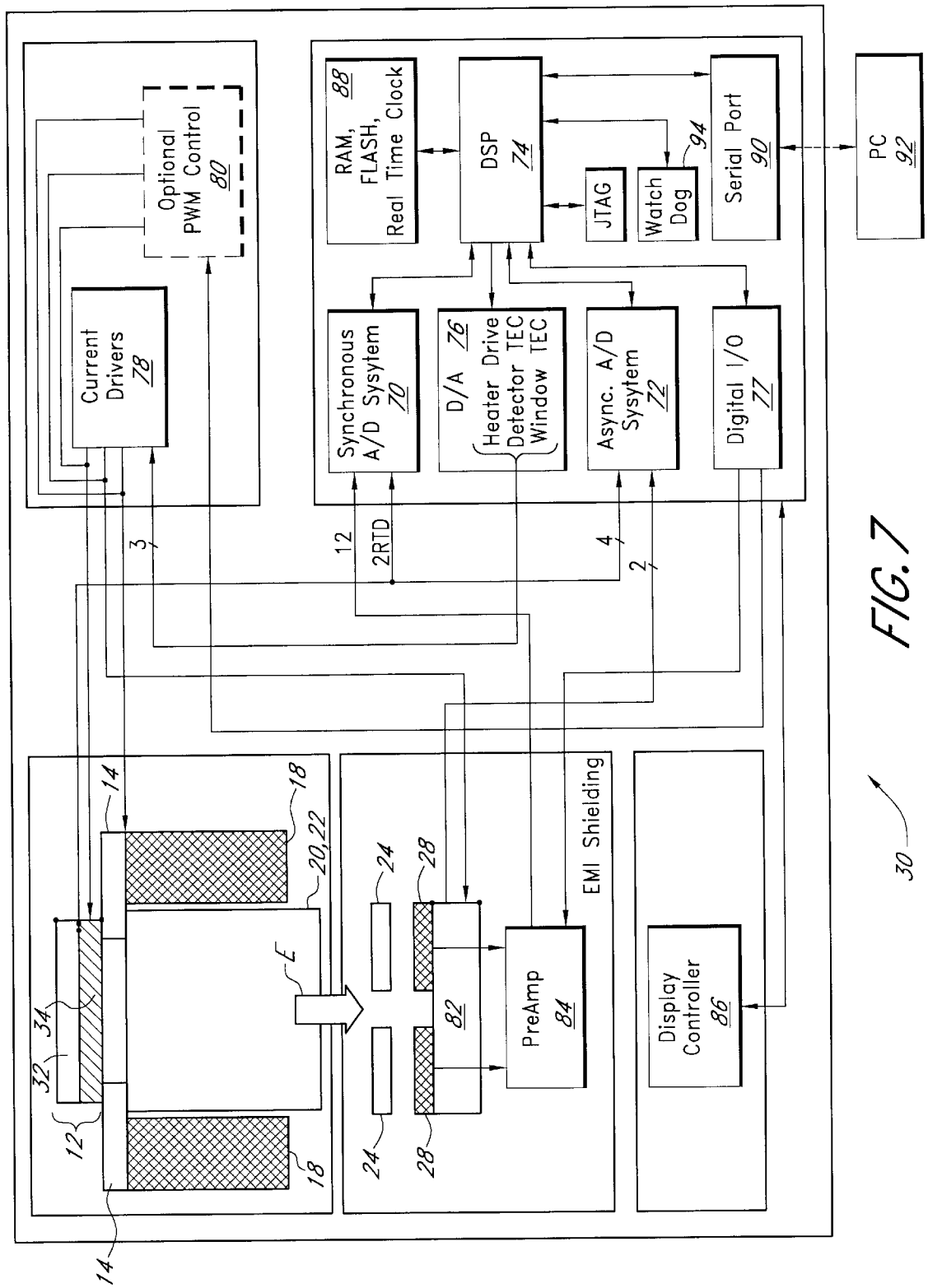
FIG. 7 is a schematic view of a control system for use with the noninvasive optical detection system.

FIG. 7 depicts the control system 30 in greater detail, as well as the interconnections between the control system and other relevant portions of the noninvasive system. The control system includes a temperature control subsystem and a data acquisition subsystem.

In the temperature control subsystem, temperature sensors (such as RTDs and/or thermistors) located in the window assembly 12 provide a window temperature signal to a synchronous analog-to-digital conversion system 70 and an asynchronous analog-to-digital conversion system 72. The A/D systems 70, 72 in turn provide a digital window temperature signal to a digital signal processor (DSP) 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital I/O device 77 to a pulse-width modulator (PWM) control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor may communicate the concentration results and/or other information to a display controller 86, which operates a display (not shown), such as an LCD display, to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a JTAG interface 96 to enable testing of the noninvasive system 10.

In one embodiment, the synchronous A/D system 70 comprises a 20-bit, 14 channel system, and the asynchronous A/D system 72 comprises a 16-bit, 16 channel system. The preamp may comprise a 12-channel preamp corresponding to an array of 12 detectors 28.

The control system may also include a serial port 90 or other conventional data port to permit connection to a personal computer 92. The personal computer can be employed to update the algorithm(s) and/or phase/concentration regression model(s) stored in the memory module 88, or to download a compilation of analyte-concentration data from the noninvasive system. A real-time clock or other timing device may be accessible by the processor 74 to make any time-dependent calculations which may be desirable to a user.

B. Invasive Systems

As mentioned above, the methods of analyte detection and analysis described herein can also be performed with invasive systems which use extracted fluid or tissue samples. A wide variety of systems for extracting and holding sample materials for analysis have been devised. Further information on invasive systems can be found in U.S. patent application Ser. No. 10/055,875, filed Jan. 21, 2002, titled REAGENT-LESS WHOLE-BLOOD GLUCOSE METER. The entire contents of this patent application are hereby incorporated by reference herein and made a part of this specification.

II. ANALYTE CONCENTRATION DEPENDENT RADIATIVE RESPONSE OF A SAMPLE MATERIAL

The detector(s) 28 of the noninvasive system 10, for example, may be used to detect the infrared energy emitted by the material sample S in various desired wavelengths. At each measured wavelength, the material sample S emits infrared energy at an intensity which is advantageously made to vary over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by measuring the time-varying intensity profiles at one or more various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the noninvasive system 10.

As shown in FIG. 8, a first reference signal P may be measured at a first reference wavelength. The first reference signal P is measured at a wavelength where water strongly absorbs (e.g., 2.9 $\mu$m or 6.1 $\mu$m). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 $\mu$m and 6.1 $\mu$m may be chosen as first reference wavelengths.

As further shown in FIG. 8, a second reference signal R may also be measured. The second signal R may be measured at a wavelength where water has very low absorbance (e.g., 3.6 $\mu$m or 4.2 $\mu$m). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

In order to determine analyte concentration, a third (analytical) signal Q is also measured. This signal is measured at an IR absorbance peak of the selected analyte. The IR absorbance peaks for glucose are in the range of about 6.5 $\mu$m to 11.0 $\mu$m. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

As further shown in FIG. 8, the signal intensities P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface. The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda)=|t_P-t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda)=|t_Q-t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to light, radiation, chemically induced heat, friction and vibration.

This methodology is not limited to the determination of phase difference. At any given time (for example, at a time $t_X$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (e.g., blood, urine or saliva) once they have been extracted from a patient. In fact, the method may be used for the measurement of in-vitro samples of virtually any kind.

In some embodiments of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (e.g., cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration. FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference $\Phi(\lambda)$ may be measured continuously throughout the test period. The phase-difference measurements may be integrated over the entire test period for an extremely accurate measure of phase difference $\Phi(\lambda)$. Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in the Assignee's U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference $\Phi(\lambda)$ and analyte concentration.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (e.g., 1 Hz) driving frequency creates a thermal gradient which penetrates deeper into the sample than the gradient created by a fast (e.g., 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 μm, after about 500 ms of exposure. Consequently, a cooling/heating cycle or driving frequency of 1 Hz provides information to a depth of about 150 μm. It has also been determined that exposure to a temperature event of 10° C. for about 167 ms creates a thermal gradient that penetrates to a depth of about 50 μm. Therefore, a cooling/heating cycle of 3 Hz provides information to a depth of about 50 μm. By subtracting the detector signal information measured at a 3 Hz driving frequency from the detector signal information measured at a 1 Hz driving frequency, one can determine the analyte concentration(s) in the region of skin between 50 and 150 μm. Of course, a similar approach can be used to determine analyte concentrations at any desired depth range within any suitable type of sample.

Figure 11:
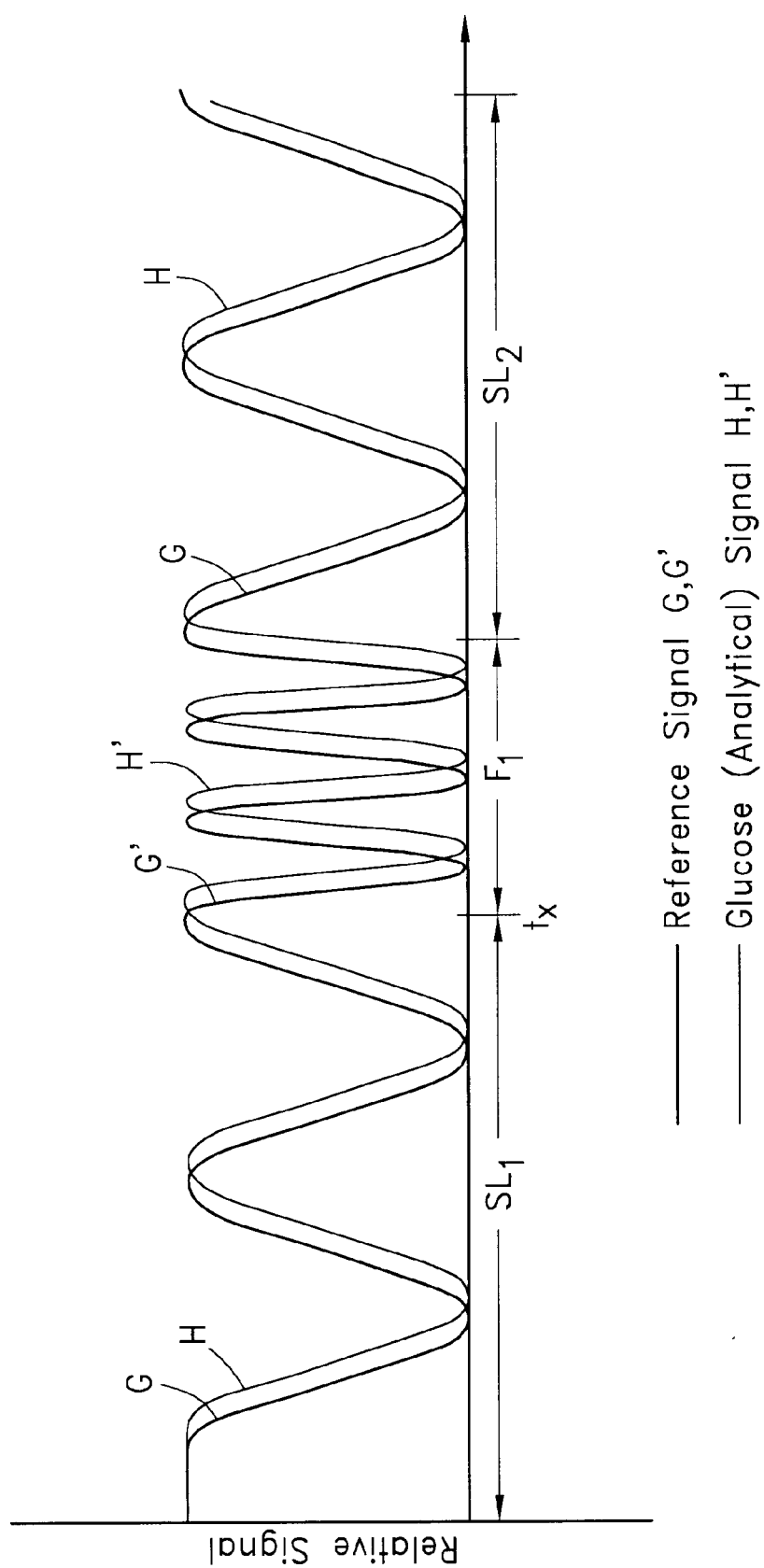
FIG. 11 depicts a fourth methodology for determining the concentration of an analyte of interest.

As shown in FIG. 11, alternating deep and shallow thermal gradients may be induced by alternating slow and fast driving frequencies. As with the methods described above, this variation also involves the detection and measurement of phase differences $\Phi(\lambda)$ between reference signals G, G' and analytical signals H, H'. Phase differences are measured at both fast (e.g., 3 Hz) and slow (e.g., 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
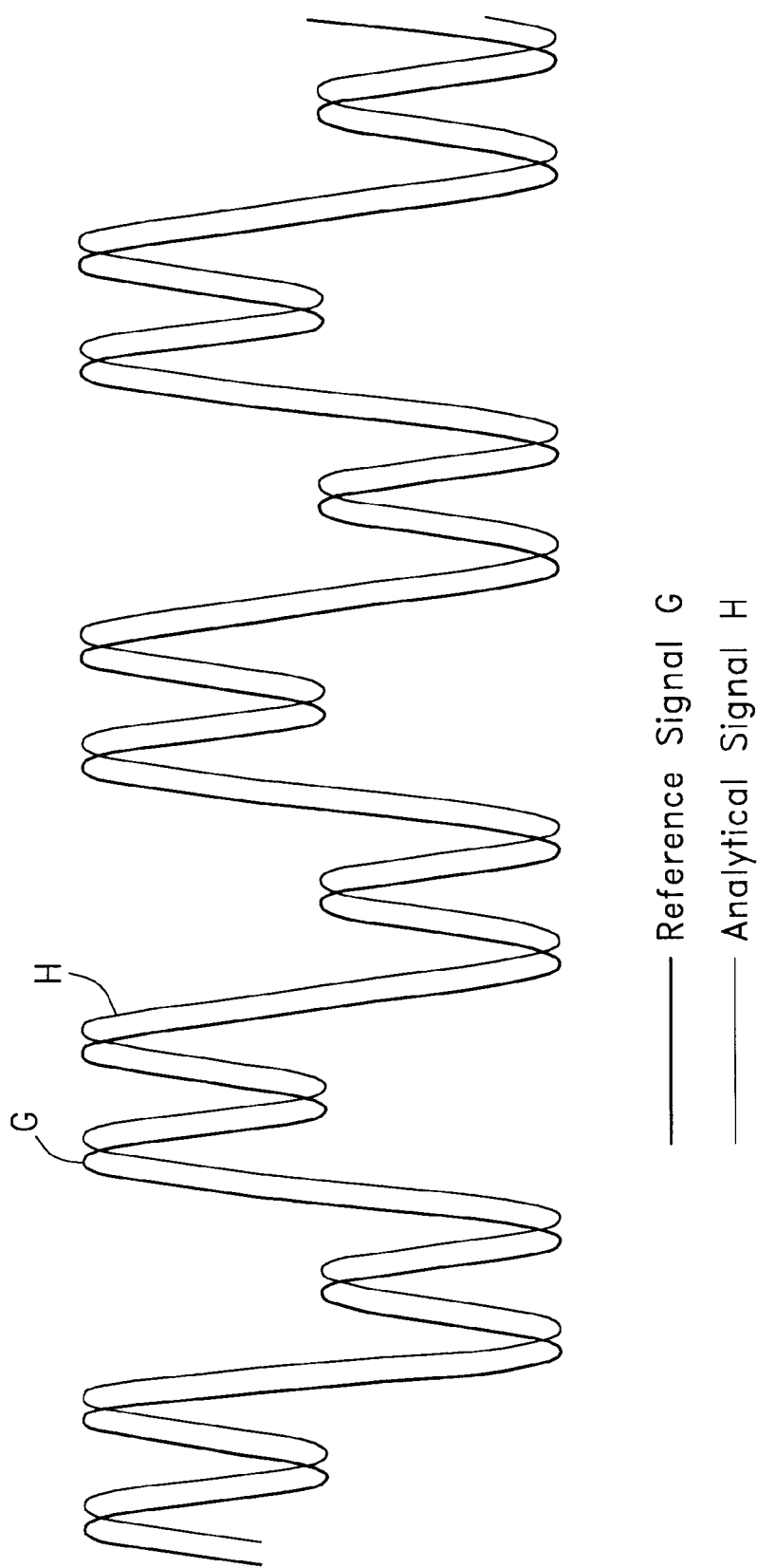
FIG. 12 depicts a fifth methodology for determining the concentration of an analyte of interest.

The driving frequencies (e.g., 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. Provisional Patent Application No. 60/336,404, filed Oct. 29, 2001, titled WINDOW ASSEMBLY; U.S. Provisional Patent Application No. 60/340,435, filed Dec. 12, 2001, titled CONTROL SYSTEM FOR BLOOD CONSTITUENT MONITOR; U.S. Provisional Patent Application No. 60/340,654, filed Dec. 12, 2001, titled SYSTEM AND METHOD FOR CONDUCTING AND DETECTING INFRARED RADIATION; U.S. Provisional Patent Application No. 60/336,294, filed Oct. 29, 2001, titled METHOD AND DEVICE FOR INCREASING ACCURACY OF BLOOD CONSTITUENT MEASUREMENT; and U.S. Provisional Patent Application No. 60/339,116, filed Nov. 7, 2001, titled METHOD AND APPARATUS FOR IMPROVING CLINICALLY SIGNIFICANT ACCURACY OF ANALYTE MEASUREMENTS. All of the above-mentioned patents, patent applications and publications are hereby incorporated by reference herein and made a part of this specification.

III. TRANSFORMATION FROM RADIATIVE PARAMETERS TO OPTICAL ABSORBANCE

A material sample comprising a medium and at least one analyte is provided. As used herein, the term "material sample" is a broad term and is used in its ordinary sense and refers, without limitation, to any collection of material which is suitable for analysis by the noninvasive system 10. For example, the material sample may comprise a tissue sample, such as a human forearm, placed against the noninvasive system 10. The material sample may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample by the noninvasive system 10. For example, the analyte(s) which may be detected by the noninvasive system 10 include but are not limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones.

Figure 13:
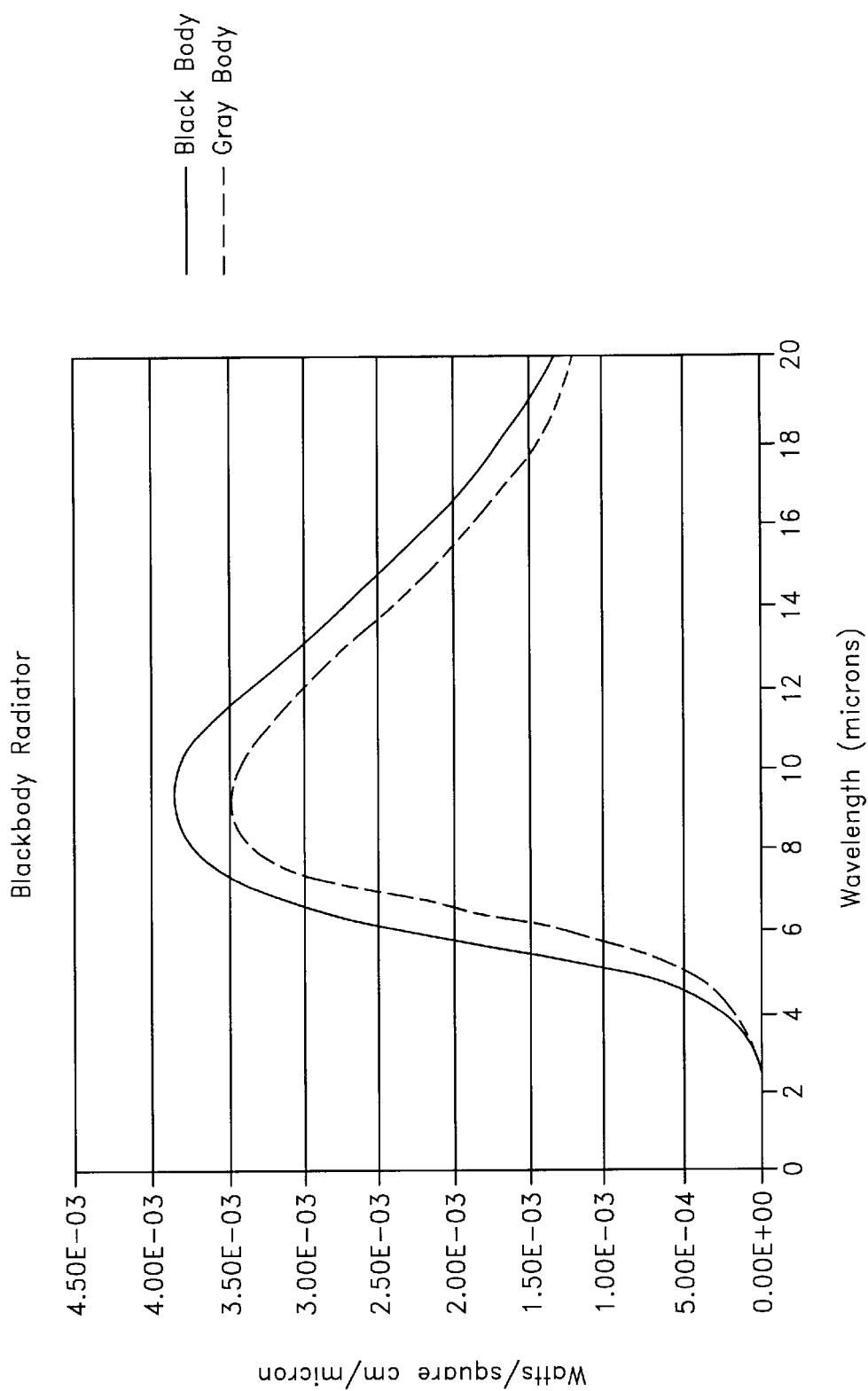
FIG. 13 is a graphical representation of the radiation distribution of a blackbody radiator in comparison with a graybody radiator.
Figure 14:
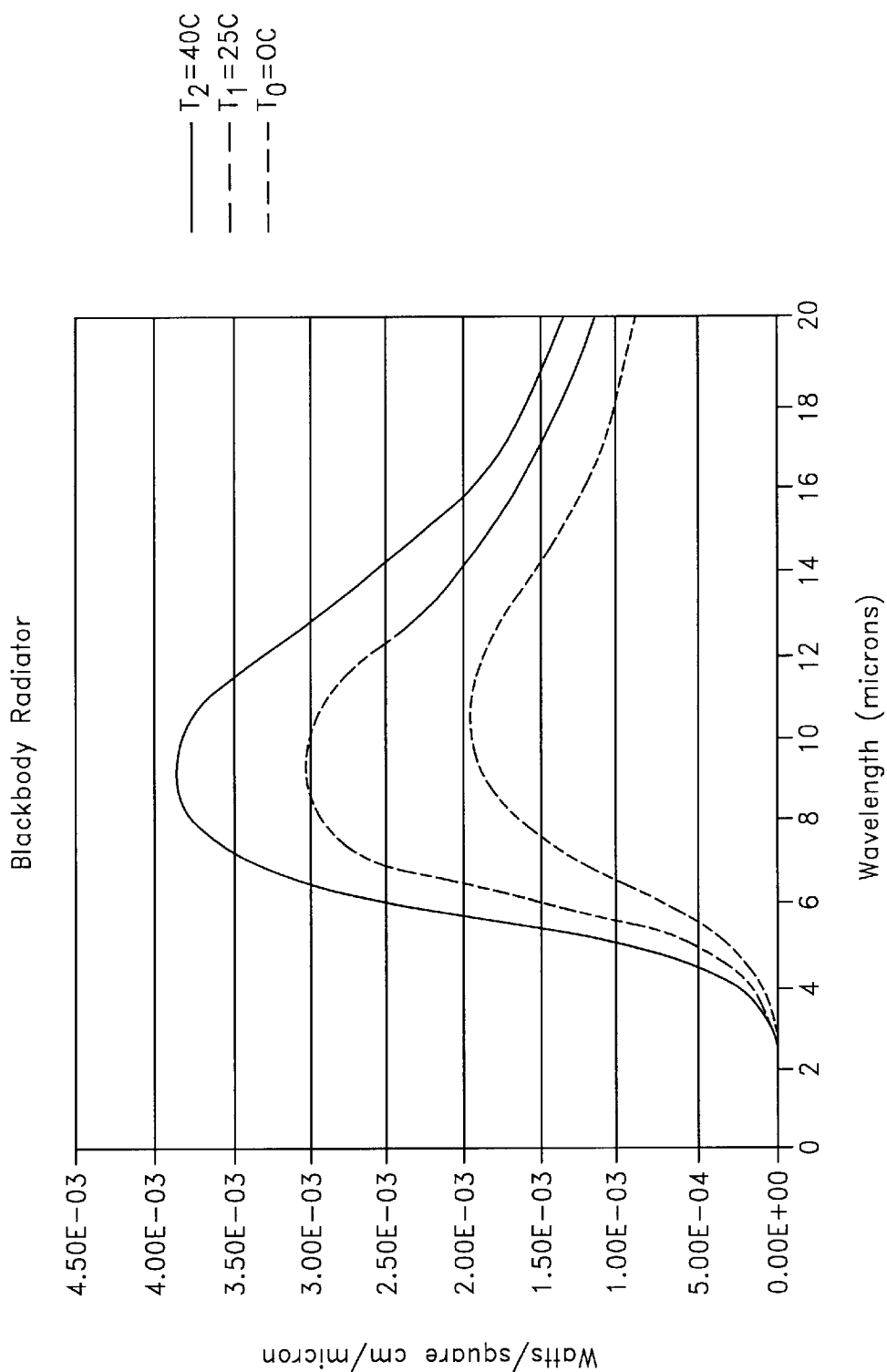
FIG. 14 is a graphical representation of the effect of temperature on spectral radiation emitted from a graybody radiator at increasing temperatures.

It is well known that all objects at a temperature greater than 0 K (Kelvin) emit electromagnetic radiation in the form of photons. Ideal blackbody radiators (objects having an emissivity coefficient $e_m=1.0$) radiate energy according to the Stefan-Boltzman Law and Planck's Equation. Additionally, many non-blackbody objects demonstrate near-blackbody radiation characteristics. For example, the spectral radiation characteristics of the human body are very similar to that of a blackbody radiator and may be described as a "graybody" distribution (for example, having an $e_m$ of about 0.9). FIG. 13 illustrates a radiation distribution of a blackbody radiator in comparison with a graybody radiator having an emissivity of about 0.9. FIG. 14 shows the effect of temperature on spectral radiation emitted from the same body at increasing temperatures $T_0$, $T_1$ and $T_2$, where the Planck radiation function is given by $$\Gamma(T(x,t),\lambda) = \frac{c_1}{\lambda^5(e^{c_2/\lambda T} - 1)}, \qquad \text{Equation 1}$$

where $c_1 = 3.784 \times 10^{-4}$ W $\mu m^2$ and $c_2 = 14,380$ $\mu m$ K.

A relationship between the modulation of the induced temperature of the surface of the sample S, for example, the skin of a human patient, and the modulation of radiation emitted from the surface S of the sample S can be defined in terms of a radiation transfer function. The radiation transfer function depends on absorbance, which, as discussed above, depends on the concentration of substances within the sample. By monitoring the phase and/or magnitude of the radiation, the absorbance at selected wavelengths can be determined. The concentration of the analyte can then be determined from the absorbance.

According to the methods taught in the above-mentioned U.S. patent application Ser. No. 09/538,164, which is incorporated by reference herein and made a part of this specification, the radiated spectral density reaching the surface, at a selected wavelength $\lambda$, can be expressed as $$P(t) = \int_0^\infty dx\, a(x) \exp\left[-\int_0^x d\xi\, \alpha(\xi)\right] \Gamma(T(x,t),\lambda), \qquad \text{Equation 2}$$

wherein $\Gamma(T(x,t),\lambda)$ is the Planck radiation function, given above. For simplicity of notation, the wavelength dependence of the IR absorbance function $a(x,\lambda)$ is not explicitly shown. The above equation for $P(t)$ assumes a semi-infinite slab of material having an IR absorbance function $a(x,\lambda)$ which is a function of depth x into the sample, and which has a time and depth varying temperature T.

It is to be noted that $P(t)$ is just a depth-weighted average of the blackbody function $\Gamma(T(x,t),\lambda)$, with a weighting function of the form, $$w(x) = \alpha(x) \exp\left[-\int_0^x d\xi\, \alpha(\xi)\right].$$

The weighting function $w(x)$ has unit area; i.e., $$\int_0^\infty dx\, \alpha(x) \exp\left[-\int_0^x d\xi\, \alpha(\xi)\right] = 1.$$

Thus, in a simple case where the sample has a temperature T which is constant with both time and depth, the above integral reduces to the usual steady state Planck radiation function at the constant temperature.

In general, when the temperature of the sample is not constant, the formula for $P(t)$ above requires a function for $T(x, t)$ to be used in the Plank radiation function in evaluating the formula. If the sample S, such as the tissue of a human patient, is in contact with a temperature-modulating device and comprises a semi-infinite medium, the temperature distribution is a function of depth x and time t. The temperature modulating device may comprise any device which applies a modulating temperature change to the surface S of the sample, including the thermal gradient spectrometer taught in the above-mentioned U.S. Pat. No. 6,198,949 or any other suitable device, including those disclosed herein. Because the sample comprises a semi-infinite medium, and ($0 \leq x < \infty$), the temperature distribution function $T(x, t)$ is subject the boundary condition that at $x=0$, $T(x, t)$ is equal to the applied temperature produced by the temperature modulating device.

The temperature distribution $T(x, t)$ within the sample S is governed by the one-dimensional heat diffusion equation, expressed as $$\frac{\partial T(x,t)}{\partial t} = \beta \frac{\partial^2 T(x,t)}{\partial x^2}, \qquad \text{Equation 3}$$

wherein $\beta$ is a coefficient of thermal diffusivity [cm$^2$/sec] of the sample S. In solving or evaluating the $P(t)$ formula, the heat diffusion equation may be solved for the temperature $T(x, t)$, and this may be then substituted for the variable T in the Planck radiation function, and the integral may then be evaluated, thus providing a relationship between the time varying radiated power P at a selected wavelength and the absorbance of the sample at that wavelength as a function of depth within the sample, given a known time varying temperature modulation at the surface of the sample. This integral may be difficult to solve in every case, but numerical techniques for example can be used to relate various parameters of radiated power P such as phase or amplitude to the IR absorbance of the medium.

In certain cases, the problem is sufficiently solvable analytically solvable so as to derive simple formulas which relate at least some radiated power parameters to sample absorbance.

Homogeneous Sample

For example, if the medium is homogenous, and the applied temperature modulation is sinusoidal, then the absorbance is not a function of x, and the temperature T as a function of x and t is an exponentially decaying sinusoid:

$$T(x, t) = T_0 + T_1(x)\cos(\omega t + \theta(x)).$$ Equation 4 wherein the depth-dependence of the magnitude $T_1(x)$ is an exponential decay in x, and the phase $\theta(x)$ is linear in x. The rates of the decay and phase delay each depend on the parameter $\gamma$, where:

$$\gamma = \sqrt{\frac{\omega}{2\beta}}.$$

where $\omega$ is the angular frequency of the temperature modulation in radians/sec.

Further approximations are also helpful in this situation. For example, if the temperature does not vary dramatically from an average temperature, the blackbody radiation function can be linearly approximated by the expansion:

$$\Gamma(T(x, t), \lambda) \approx \Gamma(T_0, \lambda) + \Gamma_T(T_0, \lambda)[T(x, t) - T_0],$$

where $$\Gamma_T(T, \lambda) = \frac{\partial \Gamma(T, \lambda)}{\partial T}$$

and $T_0$ is the average temperature of the medium.

When these substitutions and approximations are performed, it can be shown that $$\tan[\theta(\lambda)] = \frac{-\gamma}{[\alpha(\lambda) + \gamma]}$$ Equation 5 where the angle $\theta$ is the phase difference between the sinusoidal radiated power intensity P(t) (in a selected narrow wavelength band centered at wavelength $\lambda$) and the sinusoidal applied temperature modulation at the surface of the medium. Thus, this phase difference is directly related to the absorbance at that wavelength for a homogeneous sample which has a sinusoidally modulated surface temperature.

Figure 15:
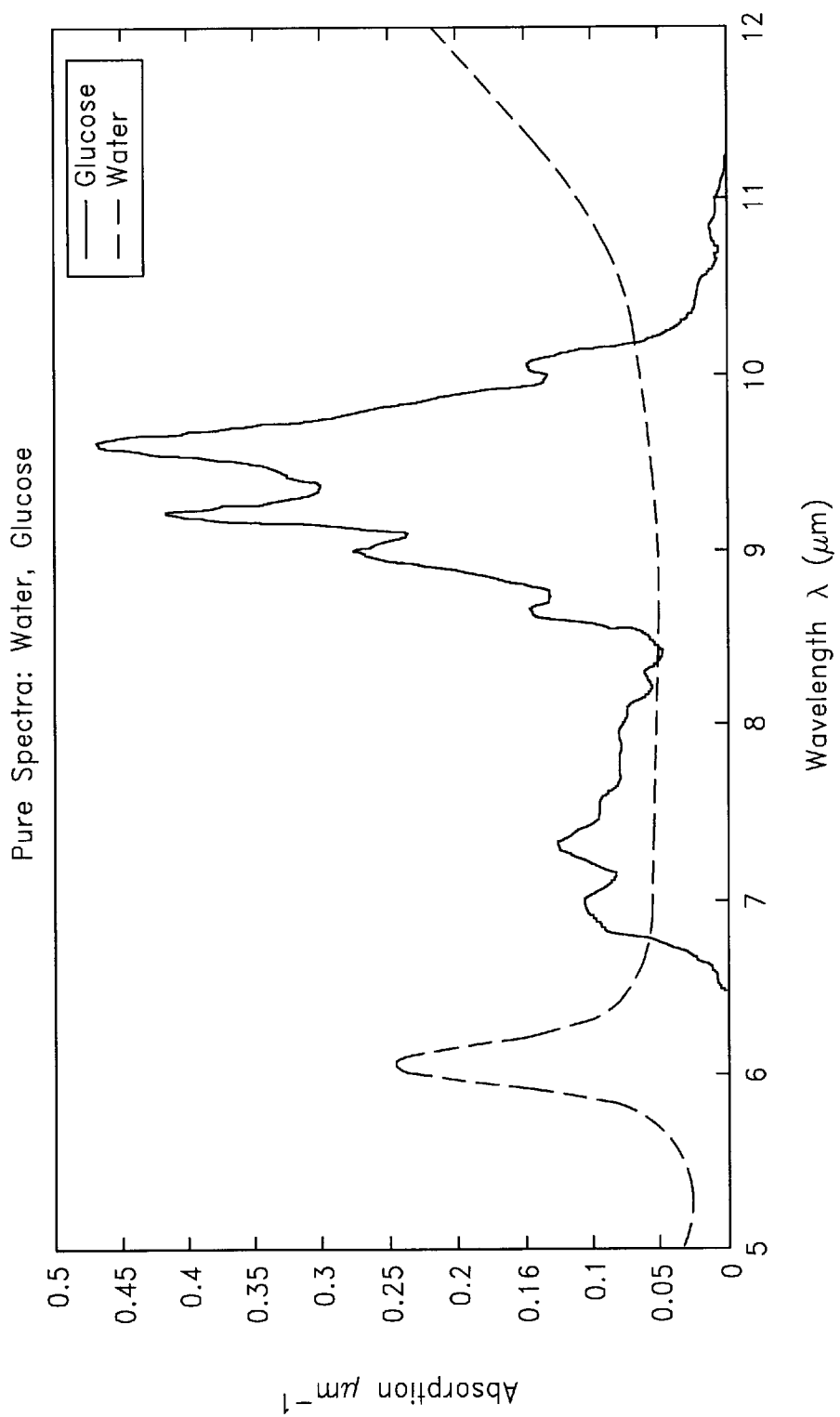
FIG. 15 shows normalized pure absorbance spectra for water and glucose.
Figure 16:
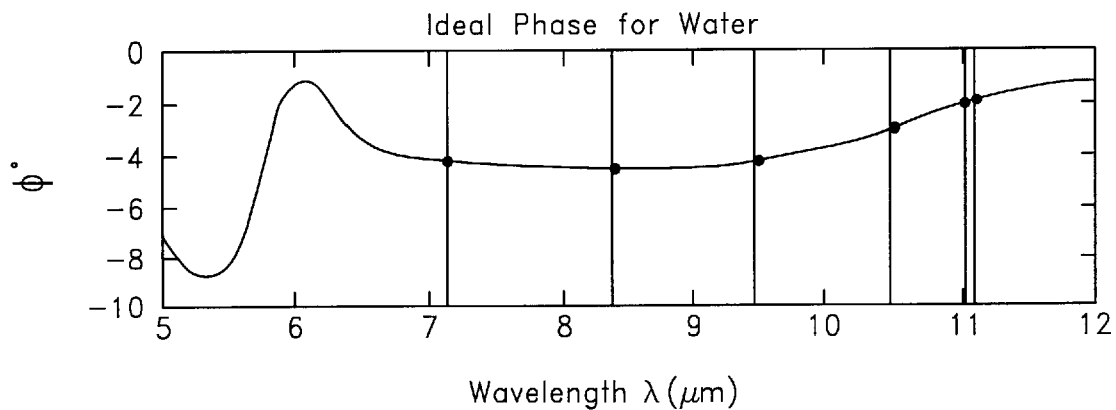
FIG. 16 is a graph illustrating a set of expected true phases for water.

FIG. 15 shows the absorption spectra as a function of wavelength from 5 to 12 micrometers for pure water and pure glucose. Given Equation 5, for a homogeneous sample of water, for example, the expected phase difference between a sinusoidal surface temperature modulation and an emitted IR power in a given wavelength band can therefore be calculated. This is shown in FIG. 16 where the absorption spectrum for water illustrated in FIG. 15 is converted to a phase spectrum for water using using Equation 5 with a value of $\gamma$ of about 0.0045.

It has been found useful to define a modified or normalized absorbance value defined as $\alpha(\lambda) = a(\lambda)/\gamma$. With this definition, normalized absorbance for a homogeneous sample can be expressed as a function of phase difference as follows:

$$\alpha(\lambda) = -[\cot(\theta(\lambda)) + 1]$$ Equation 6

It is to be noted that because $\alpha(\lambda)$ is a constant multiple of $a(\lambda)$, every linearity property enjoyed by $a(\lambda)$ is also held by $\alpha(\lambda)$. Based on this, the normalized absorbance $\alpha(\lambda)$ of the sample S, when comprising a mixture of substances, is expressible as a weighted linear sum of the normalized "pure" spectra of the constituent substances, taken in absence of one another, wherein the weights reflect the proportion of each substance within the sample S. This is expressed in the form $$\tilde{\alpha}_{TOT}(\lambda) = \sum_X [X] \tilde{\alpha}_X(\lambda),$$

in which $\alpha_{TOT}(\lambda)$ is the normalized absorbance of the sample S at wavelength $\lambda$, $\alpha_X(\lambda)$ is the normalized pure absorbance of a constituent substance within the sample S, and [X] is the proportion (or concentration) of the particular substance associated with the normalized pure absorbance $\alpha_x(\lambda)$. In one embodiment, for example, the sample S may comprise a mixture of water and glucose. The normalized spectrum for the water/glucose sample is then expressed as $$\alpha_{TOT} = [G]\alpha_G + [W]\alpha_W,$$

where $\alpha_W$ and $\alpha_G$ are the normalized pure spectra for water and glucose, respectively, and [W], [G] are the respective concentrations of water and glucose comprising the sample S. With knowledge of the values of the normalized spectrum at two wavelengths at which the individual normalized pure spectra are not in a fixed proportion to one another, a system of equations are obtained that can be solved for the concentrations [W], [G].

Glucose Concentration Measurements

A measuring device similar to that described above with reference to FIGS. 1–7 was used with the above described analysis techniques to measure glucose concentrations in a set of five sample solutions having glucose concentrations of 0, 75, 125, 250, and 500 mg/dL glucose. In these experiments, the temperature was modulated between about 25 and 40 degrees C. at a rate of 0.9375 Hz or 5 radians/sec. The phase difference between the temperature modulation and the emitted IR radiation was determined at about 9.6 and 8.4 micrometer wavelengths. Total absorbance was calculated using Equation 5 with a $\gamma$ of about 0.0045. Glucose concentrations were computed by separating the contributions to the total absorbance of the glucose and the water as described above, and determining glucose concentration with the known glucose absorbance as a function of concentration. Each measurement was performed twice on each sample solution. The results appear in the following Table:

| Actual Glucose Concentration (mg/dL) | First Measured Glucose Concentration (mg/dL) | Second Measured Glucose Concentration (mg/dL) |
|---|---|---|
| 0 | 0 | 2 |
| 62 | 67 | 61 |

-continued

| Actual Glucose Concentration (mg/dL) | First Measured Glucose Concentration (mg/dL) | Second Measured Glucose Concentration (mg/dL) |
|---|---|---|
| 125 | 129 | 114 |
| 250 | 252 | 245 |
| 500 | 503 | 510 |

As shown in this Table, with the exception of two values the errors are 5 mg/dL or less in absolute value. The RMS error is 3.13 mg/dL.

Layered Sample

Instead of being homogeneous, the sample S may comprise a plurality of layers. For example, human skin comprises a thin layer of stratum corneum approximately 10 $\mu$m thick which covers the surface of the skin and contains no fluid. Underlying the stratum corneum is a layer of epidermis approximately 100 $\mu$m thick. The epidermis contains interstitial and intracellular fluids that are important because the fluids suspend analyte materials of interest, such as glucose. Beneath the epidermis lies a thick layer of derma, which also contains fluids and suspended blood analytes such as glucose. Within each of these layers thermal and optical characteristics can be considered uniform. For such a layered sample S, the formula for P(t) may be evaluated by using the boundary condition at x=0, as well as boundary conditions at the surfaces of the layers within the sample S. Using a model of layered skin, therefore, parameters of the received IR power can also be related to sample absorbance, thus measuring analyte concentrations within living tissue in a non-invasive manner.

In one embodiment, the process described herein for computing an absorption is implemented in a noninvasive analyte detection system such as the noninvasive system 10 disclosed above. Where employed in the noninvasive system 10 the process for computing the normalized absorption spectrum may reside as a data processing algorithm or program instructions within memory accessible by the signal processor 74/260. It is contemplated that the signal processor 74/260 executes the algorithm/program containing the computation process to transform radiated power parameters such as phase data into the absorption values of analytical chemistry with which analyte concentrations can be determined as disclosed in various embodiments herein.

It will be appreciated that the physical nature of the IR detectors and the details of the measurement process may result in the need to make system and measurement adjustments or calibrations in order to produce a phase difference value $\theta$ from an actual measured IR radiation parameter. This process is described below for one embodiment of an analyte measurement system and technique.

Calibration Process

As used herein, the term "true phase" refers to an actual phase offset between the temperature modulation at the surface of the sample and the modulation of the radiated IR power emitted from the sample at a selected wavelength. The term "observed phase" refers to a raw numerical value which has been measured by one or more of the detectors 28. To produce the true phase from the observed phase, the observed phase is advantageously subjected to a calibration process. Producing an approximation to the true phase on the basis of actual detector output is affected by several factors. A phase offset may be introduced by the measurement process. In some embodiments of the invention, the observed phase is defined with reference to an internally generated reference signal that may itself be out of phase with the actual temperature modulation. Furthermore, individual detectors 28 often possess different characteristic phase offsets. In addition, these phase offsets may tend to wander, or drift, over time. In one embodiment, the calibration process comprises an offset method for correcting any individual phase deviations from the ideal and a drift correction method for substantially eliminating temporal drift which occurs during the data collection process.

1. Detector Phase Offset

Figure 17:
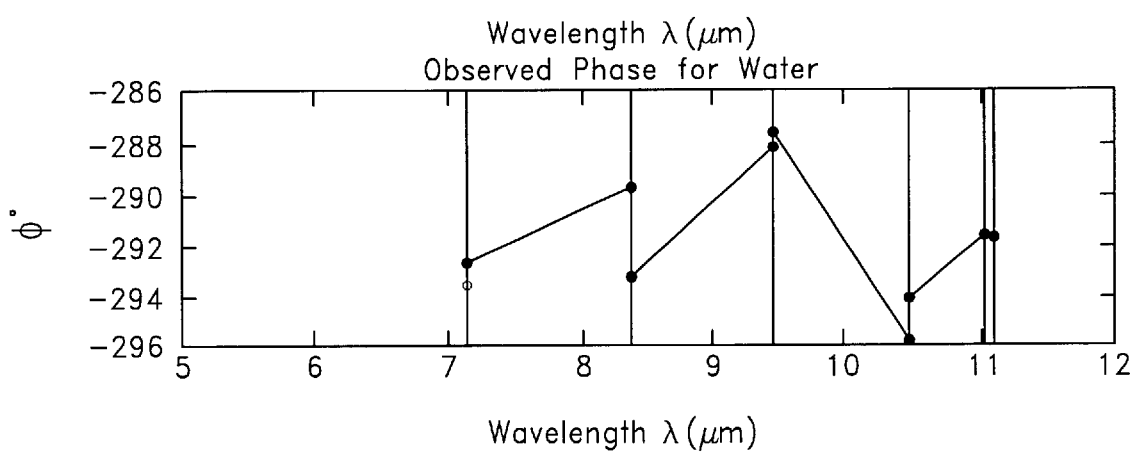
FIG. 17 is a graph illustrating a set of experimentally measured phases for a mixture of water and glucose.

In one offset correction method, a set of "observed" phases $\theta_\lambda^{REF}$ is experimentally obtained for a reference material. The set of observed phases $\theta_\lambda^{REF}$ may comprise, for example, the data output of the array of detectors 28. The reference material preferably has well known spectral and thermal properties, and thus has a well defined normalized absorption spectrum, $\alpha_\lambda^{REF}$ It is to be understood that the superscripts on $\theta_\lambda^{REF}$, $\alpha_\lambda^{REF}$ represent the reference material and the subscripts represent a particular wavelength at which measurements are performed. It is contemplated that each of the observed phases $\theta_\lambda^{REF}$ corresponds to a specific wavelength $\lambda$ at which measurements are taken. FIG. 17 illustrates a set or, spectrum, of observed phases $\theta_\lambda^{REF}$ measured by the detectors 28 at several wavelengths, $\lambda$, for a reference sample comprising pure water. In FIG. 17, each point represents a measurement from one detector. As can be seen in this Figure, more than one detector may be measuring the same wavelength. The data set shown in FIG. 17 was generated from 10 different detectors 28 at six different wavelengths. It can be seen that in addition to a relatively large average offset from the expected phases shown in FIG. 16, different detectors at the same wavelength can also differ in their "observed" phases. Next, the expression for the normalized absorption spectrum $\alpha_\lambda^{REF}$ is used for the reference material to calculate a spectrum of expected true phases $\theta_\lambda^{REF}$, which corresponds to the set of observed phases $\theta_\lambda^{REF}$. This is carried out by determining a value of the normalized absorption spectrum $\alpha_\lambda^{REF}$ for each wavelength $\lambda$ at which measurements are taken, and then inserting the resulting values into the expression for the true phase:

$$\tilde{\theta}_\lambda^{REF} = -\tan^{-1}\left[\frac{1}{\tilde{\alpha}_\lambda^{REF} + 1}\right].$$

FIG. 16 described above shows a spectrum of expected true phases $\theta_\lambda^{REF}$ for pure water, computed at the same wavelengths at which the observed phases $\theta_\lambda^{REF}$ of FIG. 17 were measured. The difference between each true phase $\theta_\lambda^{REF}$ and the corresponding observed phase $\theta_\lambda^{REF}$ comprises an offset value, which is computed (for each wavelength $\lambda$ at which measurements are performed) by using the expression $$\theta_\lambda^{OFFSET} = \tilde{\theta}_\lambda^{REF} - \theta_\lambda^{REF}.$$

Using this expression for a set of wavelengths $\lambda$ results in a spectrum of offset values $\theta_\lambda^{OFFSET}$. Adding each offset value $\theta_\lambda^{OFFSET}$ to the corresponding observed phase $\theta_\lambda^{REF}$ results in a corrected phase $\theta_\lambda^{CORR}$, which is substantially equivalent to the corresponding expected true phase $\theta_\lambda$. More generally, for each detector 28 with which measurements are taken, the observed phase $\theta_{\lambda,n}$ is corrected by adding the appropriate offset value $\theta_{\lambda,n}^{OFFSET}$:

$$\theta_{\lambda,n}^{CORR} = \theta_{\lambda,n} + \theta_{\lambda,n}^{OFFSET}.$$

wherein the subscript n represents the nth detector that is used during a measurement run, and wherein the offset values $\theta_\lambda^{OFFSET}$ remain constant throughout the measurement run. Upon adding the appropriate offset values to the observed phases $$\theta_\lambda^{REF}$$

of FIG. 17, the spectrum of observed phases illustrated in FIG. 17 will become substantially the same as the ideal phase $\theta_\lambda$ spectrum illustrated in FIG. 16.

2. Temporal Drift

Figure 18:
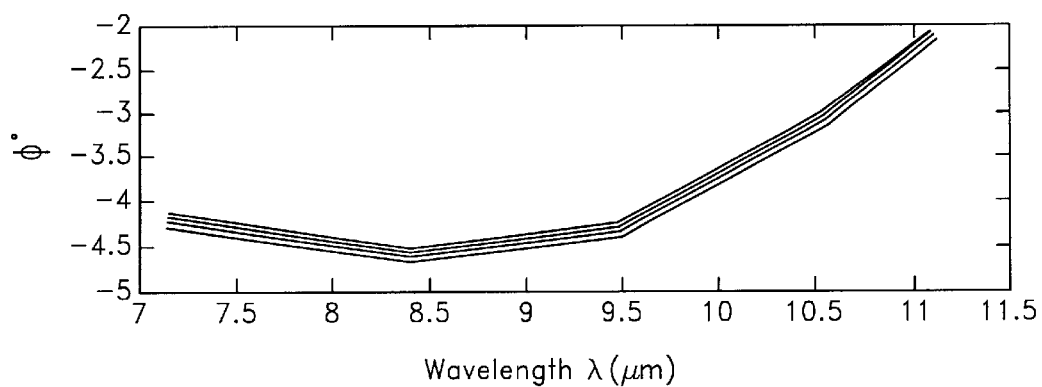
FIG. 18 is a graphical illustration of system drift within in the phase spectrum of water.

As mentioned above, a drift correction method may also be utilized to facilitate a substantial elimination of temporal drift which occurs during the data collection process. System drift is known to be substantially the same across all wavelengths (i.e., the detectors 28) during an observation, but varies from one observation to another. FIG. 18 illustrates a system drift in the phase spectrum of water. In the embodiment illustrated in FIG. 18, the phase spectrum for water comprises ten sets of phase data (denoted by the ten lines in the graph) obtained during ten observations, wherein each set of phase data has been corrected with the above-discussed offset method. The system drift is evidenced by the lack of coincidence among the phase lines in the graph of FIG. 18. In one embodiment, the tendency of a full system of detectors 28 to drift or wander in phase over time can be mitigated if it is known that one particular detector results in a phase that remains stationary and has a constant value during the data collection process. For instance, a stationary phase may result if one wavelength is known never to penetrate to an appreciable depth within the sample, or if one of the detectors 28 is adjusted such that its signal is constrained to originate from the surface S of the sample. Hereinafter, the term "stationary wavelength" is used in reference to a particular wavelength for which the true phase $\theta_\lambda$ remains stationary over a time span much greater than the duration of the full set of observations.

In one embodiment, the stationary wavelength comprises a reference phase. The detector 28 observing the stationary wavelength can be "drift corrected" by adjusting the reference phase such that it remains constant during all observations. A drift correction $\delta_n$ is obtained by using the expression $$\delta_n = \theta_0^{STAT} - \theta_n^{STAT},$$

where the superscripts indicate the stationary wavelength, and the subscripts 0, n represent the initial observation and the nth observation, respectively. Upon adding the drift correction $\delta_n$ to the reference phase, the resulting drift-corrected reference phase remains fixed at its initial value. Next, the mutual drift of the full system of detectors 28 is corrected for each observation by adding the drift correction $\delta_n$ to each phase $\theta_n$:

$$\theta_n^{DC} = \theta_n + \delta_n.$$

Figure 19:
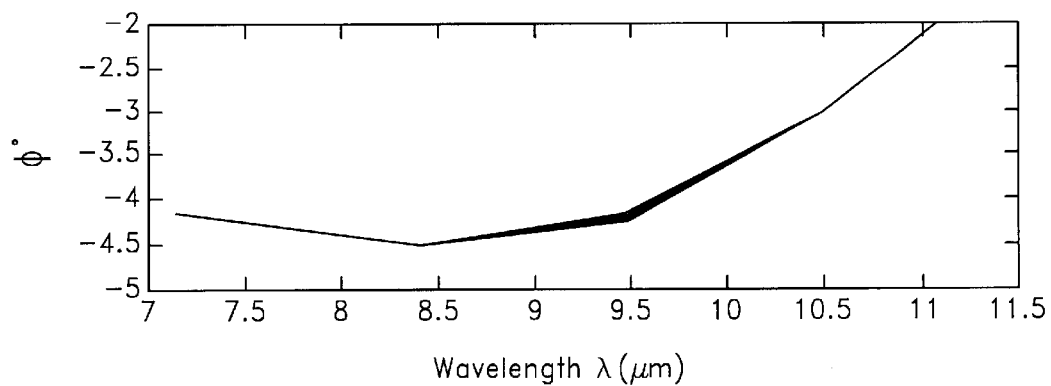
FIG. 19 illustrates the phase data after having been subjected to a drift correction method.

In this expression, the superscript indicates that the phase is drift corrected, the subscripts denote the nth observation, and $\theta_n$ represents the full array of phases across all the detectors 28 for the nth observation. FIG. 19 illustrates the phase data of FIG. 18 after having been subjected to the drift correction method. As shown in FIG. 19, the ten phase lines are coincident, with the exception of a minor deviation at a wavelength of about 9.5 µm. Upon referring to FIG. 20, it is to be noted that glucose strongly absorbs at about 9.5 µm, thus giving rise the phase deviation shown in FIG. 19.

In one embodiment, the calibration process is implemented in a noninvasive analyte detection system such as the noninvasive system 10 disclosed herein. Where employed in the noninvasive system 10, the calibration process may reside as a data processing algorithm or program instructions within memory accessible by the signal processor 74/260. It is contemplated that the signal processor 74/260 executes the algorithm/program containing the calibration process to transform raw, measured phase spectra output by the detectors 28 into adjusted, ideal phase spectra as disclosed in various embodiments above.

Using the above-discussed offset and drift correction methods transforms a set of raw observed phases to a set of substantially ideal phases. Such a transformation is expressed as $$\theta_\lambda^{RAW} \rightarrow \theta_\lambda^{RAW} + \theta_\lambda^{OFFSET} + \delta_n.$$

Using this transformation in the expression for the normalized absorption spectrum $\alpha(\lambda)$ gives $$\tilde{\alpha}(\lambda) = -\lfloor \cot(\theta_\lambda^{RAW} + \varphi_\lambda^{OFFSET} + \delta_n) + 1 \rfloor.$$

Figure 20:
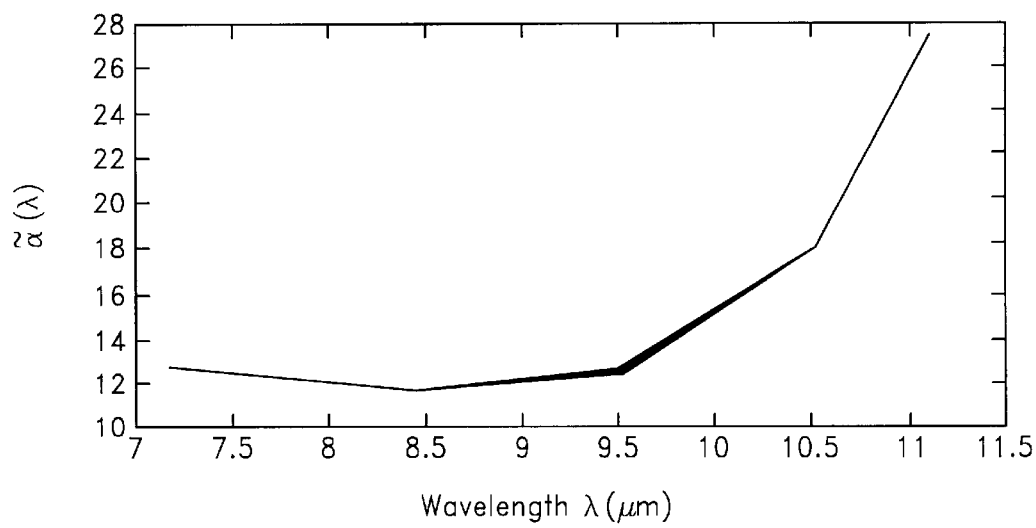
FIG. 20 is a graph of normalized absorption spectra plotted as a function of wavelength for the water/glucose mixture of FIG. 20.

This expression provides a direct relationship between raw, experimentally observed phases and the classical absorption spectrum of analytical chemistry. FIG. 20 illustrates a graph of the normalized absorption spectrum $\alpha(\lambda)$ plotted as a function of wavelength $\lambda$ for the water/glucose sample discussed above with reference to FIG. 19.

In one embodiment, the above-discussed process for transforming/correlating phase data to absorption is implemented in a noninvasive analyte detection system such as the noninvasive system 10 disclosed herein. Where employed in the noninvasive system 10, the transformation process may reside as a data processing algorithm or program instructions within memory accessible by the signal processor 74/260. It is contemplated that the signal processor 74/260 executes the algorithm/program containing the transformation process to convert raw, measured phase spectra output by the detectors 28 into absorption spectra whereby analyte concentrations may be determined as disclosed in various embodiments above.

It is contemplated that the methods disclosed herein can be used to improve the accuracy of a wide variety of devices, such as, but not limited to, detectors which analyze the constituents of blood withdrawn from a patient; noninvasive measurement devices of any type, including thermal gradient spectrometers of the type disclosed herein or in the above-mentioned U.S. Pat. No. 6,198,949 or U.S. patent application Ser. No. 09/538,164; implantable and/or subcutaneous measurement devices; devices which measure glucose levels continuously and devices which measure glucose levels intermittently. In a presently preferred embodiment, the disclosed methods are used with a thermal gradient spectrometer to increase the accuracy of its measurement of the concentration of glucose in the bodily fluids of a patient.

Although preferred embodiments and methods have been described in detail, certain variations and modifications thereof will be apparent to those skilled in the art, including embodiments and/or methods that do not provide all of the features and benefits described herein. Accordingly, the scope of the above-discussed embodiments and methods is not to be limited by the illustrations or the foregoing descriptions thereof, but rather solely by appended claims.

What is claimed is:

1. A method for determining a concentration of an analyte within a material sample, said method comprising:
   inducing said material sample to emit electromagnetic energy in a time-varying manner;
   measuring, at at least one wavelength, said induced electromagnetic energy emitted by said material sample;
   determining a phase of said electromagnetic energy;
   converting said phase into an absorption value; and
   determining said concentration of said analyte based at least in part on said absorption.

2. The method of claim 1, wherein converting said phase into an absorption value comprises converting said phase into a normalized absorption.

3. The method of claim 2, wherein determining said concentration of said analyte based on said absorption comprises determining said concentration of said analyte based on said normalized absorption.

4. The method of claim 1, wherein measuring comprises analyzing said material sample with an optical measurement system.

5. The method of claim 4, wherein said optical measurement system comprises an array of wavelength-specific detectors.

6. The method of claim 4, further comprising correcting said optical measurement system for temporal variations in performance.

7. The method of claim 1, wherein inducing said material sample to emit electromagnetic energy in a time-varying manner comprises inducing a periodically modulated thermal gradient in said material sample.

8. The method of claim 1, wherein said electromagnetic energy comprises infrared radiation.

9. A method for determining a concentration of an analyte within a material sample, said method comprising:
   determining at least a portion of a phase spectrum based on electromagnetic energy emitted by said material sample;
   converting said at least a portion of said phase spectrum into at least a portion of an absorption spectrum; and
   determining said concentration based on said at least a portion of said absorption spectrum.

10. The method of claim 9, wherein converting said phase spectrum into an absorption spectrum comprises converting said phase spectrum into a normalized absorption spectrum.

11. The method of claim 10, wherein determining said concentration of said analyte based on said absorption spectrum comprises determining said concentration of said analyte based on said normalized absorption spectrum.

12. The method of claim 9, wherein said phase spectrum comprises an ideal phase spectrum.

13. The method of claim 9, wherein determining a phase spectrum comprises analyzing said material sample with an optical measurement system.

14. The method of claim 13, wherein said optical measurement system comprises an array of wavelength-specific detectors.

15. The method of claim 13, further comprising correcting said optical measurement system for temporal variations in performance.

16. The method of claim 9, further comprising inducing a periodically modulated thermal gradient in said material sample.

17. The method of claim 9, wherein said electromagnetic energy comprises infrared radiation.

18. An analyte detection system comprising:
   a detector array;
   a processing circuit in communication with said detector array; and
   a module executable by said processing circuit whereby said processing circuit converts a phase spectrum, said phase spectrum based on electromagnetic energy emitted by a material sample and measured by said detector array, into an absorption spectrum and determines a concentration of an analyte within said material sample based on said absorption spectrum.

19. The analyte detection system of claim 18, further comprising means for inducing said material sample to emit electromagnetic energy in a time-varying manner, said means for inducing being in communication with said processing circuit.

20. The analyte detection system of claim 18, further comprising means for inducing a periodically modulated thermal gradient in said material sample, said means for inducing being in communication with said processing circuit.

21. The analyte detection system of claim 18, wherein said electromagnetic energy comprises infrared radiation.

22. A method of estimating analyte concentration in a sample comprising:
   applying a time varying temperature to a portion of a sample;
   measuring time varying infrared radiation intensity received from said sample in at least one wavelength band;
   calculating an absorption coefficient $\alpha$ in said wavelength band based at least in part on said time varying infrared radiation intensity received from said sample.

23. The method of claim 22, additionally comprising calculating a phase difference $\theta$ between said time varying temperature and said time varying infrared radiation intensity and calculating said absorption coefficient $\alpha$ based at least in part on said phase difference $\theta$.

24. The method of claim 23, wherein said absorption coefficient is calculated from said phase difference according to the formula $$\tan[\theta(\lambda)] = \frac{-\gamma}{[\alpha(\lambda) + \gamma]},$$

wherein $\gamma = \overline{\omega/2\beta}$, wherein $\omega$ is the angular modulation frequency in radians/sec, and $\beta$ is the coefficient of thermal diffusivity of the sample.

* * * * *